United States Patent
Nguyen

(10) Patent No.: US 10,524,648 B2
(45) Date of Patent: Jan. 7, 2020

(54) FEATURES TO PREVENT CROSS-CONTAMINATION OF ENDOSCOPE FROM REPROCESSING SYSTEM

(71) Applicant: ASP Global Manufacturing GmbH, Schaffhausen (CH)

(72) Inventor: Nick N. Nguyen, Silverado, CA (US)

(73) Assignee: ASP GLOBAL MANUFACTURING GMBH, Schaffhausen (CH)

( * ) Notice: Subject to any disclaimer, the term of this patent is extended or adjusted under 35 U.S.C. 154(b) by 0 days.

(21) Appl. No.: 15/230,661

(22) Filed: Aug. 8, 2016

(65) Prior Publication Data
US 2018/0035880 A1    Feb. 8, 2018

(51) Int. Cl.
| | | |
|---|---|---|
| *A61B 1/12* | (2006.01) | |
| *A61L 2/26* | (2006.01) | |
| *A61L 2/18* | (2006.01) | |
| *B08B 3/08* | (2006.01) | |
| *B08B 3/14* | (2006.01) | |
| *B08B 9/023* | (2006.01) | |
| *B08B 9/032* | (2006.01) | |

(52) U.S. Cl.
CPC .............. *A61B 1/123* (2013.01); *B08B 3/08* (2013.01); *B08B 3/14* (2013.01); *B08B 9/023* (2013.01); *B08B 9/0321* (2013.01)

(58) Field of Classification Search
CPC .............. A61L 2/18; A61B 1/123; B01L 7/02
USPC ........................................................ 422/292
See application file for complete search history.

(56) References Cited

U.S. PATENT DOCUMENTS

| | | |
|---|---|---|
| 6,986,736 B2 | 1/2006 | Williams et al. |
| 7,479,257 B2 | 1/2009 | Nguyen et al. |
| 7,686,761 B2 | 3/2010 | Jackson et al. |
| 8,246,909 B2 | 8/2012 | Williams et al. |

(Continued)

FOREIGN PATENT DOCUMENTS

| | | |
|---|---|---|
| CN | 101366959 A | 2/2009 |
| EP | 1481692 A1 | 12/2004 |

(Continued)

OTHER PUBLICATIONS

Extended European Search Report for EP Patent Application Serial No. 17185157.9, dated Dec. 18, 2017, 10 pages.

*Primary Examiner* — Kevin Joyner
*Assistant Examiner* — Holly M Mull
(74) *Attorney, Agent, or Firm* — Frost Brown Todd LLC

(57) ABSTRACT

A reprocessing system includes a decontamination basin, a lid, a cleaning assembly, an exterior body, and an actuating panel assembly. The lid is configured to enclose the interior surface of the decontamination basin in a closed configuration. The lid and an interior surface of the decontamination basin are configured to cooperate to house a medical device when in the lid is in the closed configuration. The cleaning assembly is operable to clean a medical device housed in the decontamination basin. The actuating panel assembly is configured to transition between a withdrawn position and an extended position. The actuating panel assembly is configured to be enclosed by the lid and the interior surface of the decontamination basin in the withdrawn position. The actuating panel assembly is configured to extend above a portion of the exterior body while the actuating panel assembly is in the extended position.

20 Claims, 16 Drawing Sheets

(56) References Cited

U.S. PATENT DOCUMENTS

| | | | | |
|---|---|---|---|---|
| 8,584,837 B1* | 11/2013 | Mather | ............... | A45D 27/24 134/157 |
| 2009/0044845 A1* | 2/2009 | Cui | ............... | A61B 1/123 134/56 R |
| 2009/0065034 A1* | 3/2009 | Suzuki | ............... | A61B 1/123 134/56 R |

FOREIGN PATENT DOCUMENTS

| | | | |
|---|---|---|---|
| EP | 1839683 | A1 | 10/2007 |
| EP | 1875856 | A1 | 1/2008 |

* cited by examiner

FEATURES TO PREVENT CROSS-CONTAMINATION OF ENDOSCOPE FROM REPROCESSING SYSTEM

BACKGROUND

The below discussion relates to the reprocessing (i.e., decontamination) of endoscopes and other instruments that are used in medical procedures. In particular, the below discussion relates to an apparatus and a method that may be used to reprocess a medical device such as an endoscope after the medical device has been used in a first medical procedure, such that the medical device may be safely used in a subsequent medical procedure. While the below discussion will speak mainly in terms of an endoscope, it should be understood that the discussion may also equally apply to certain other medical devices.

An endoscope may have one or more working channels or lumens extending along at least a portion of the length of the endoscope. Such channels may be configured to provide a pathway for passage of other medical devices, etc., into an anatomical region within a patient. These channels may be difficult to clean and/or disinfect using certain primitive cleaning and/or disinfecting techniques. Thus, the endoscope may be placed in a reprocessing system that is particularly configured to clean endoscopes, including the channels within endoscopes. Such an endoscope reprocessing system may wash and disinfect the endoscope. Such an endoscope reprocessing system may include a basin that is configured to receive the endoscope, with a pump that flows cleaning fluids over the exterior of the endoscope within the basin. The system may also include ports that couple with the working channels of the endoscope and associated pumps that flow cleaning fluids through the working channels of the endoscope. The process executed by such a dedicated endoscope reprocessing system may include a detergent washing cycle, followed by a rinsing cycle, followed by a sterilization or disinfection cycle, followed by another rinsing cycle. The sterilization or disinfection cycle may employ disinfection solution and water rinses. The process may optionally include an alcohol flush to aid displacement of water. A rinsing cycle may be followed by an air flush for drying and storage.

Examples of systems and methods that may be used to reprocess a used endoscope are described in U.S. Pat. No. 6,986,736, entitled "Automated Endoscope Reprocessor Connection with Integrity Testing," issued Jan. 17, 2006, the disclosure of which is incorporated by reference herein; U.S. Pat. No. 7,479,257, entitled "Automated Endoscope Reprocessor Solution Testing," issued Jan. 20, 2009, the disclosure of which is incorporated by reference herein; U.S. Pat. No. 7,686,761, entitled "Method of Detecting Proper Connection of an Endoscope to an Endoscope Reprocessor," issued Mar. 30, 2010, the disclosure of which is incorporated by reference herein; and U.S. Pat. No. 8,246,909, entitled "Automated Endoscope Reprocessor Germicide Concentration Monitoring System and Method," issued Aug. 21, 2012, the disclosure of which is incorporated by reference herein. An example of a commercially available endoscope reprocessing system is the EVOTECH® Endoscope Cleaner and Reprocessor (ECR) by Advanced Sterilization Products of Irvine, Calif.

While a variety of systems and methods have been made and used to reprocess medical devices, it is believed that no one prior to the inventor(s) has made or used the technology as described herein.

BRIEF DESCRIPTION OF THE DRAWINGS

It is believed the present invention will be better understood from the following description of certain examples taken in conjunction with the accompanying drawings, in which like reference numerals identify the same elements and in which.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Medical Device Reprocessing Apparatus

Figure 1:
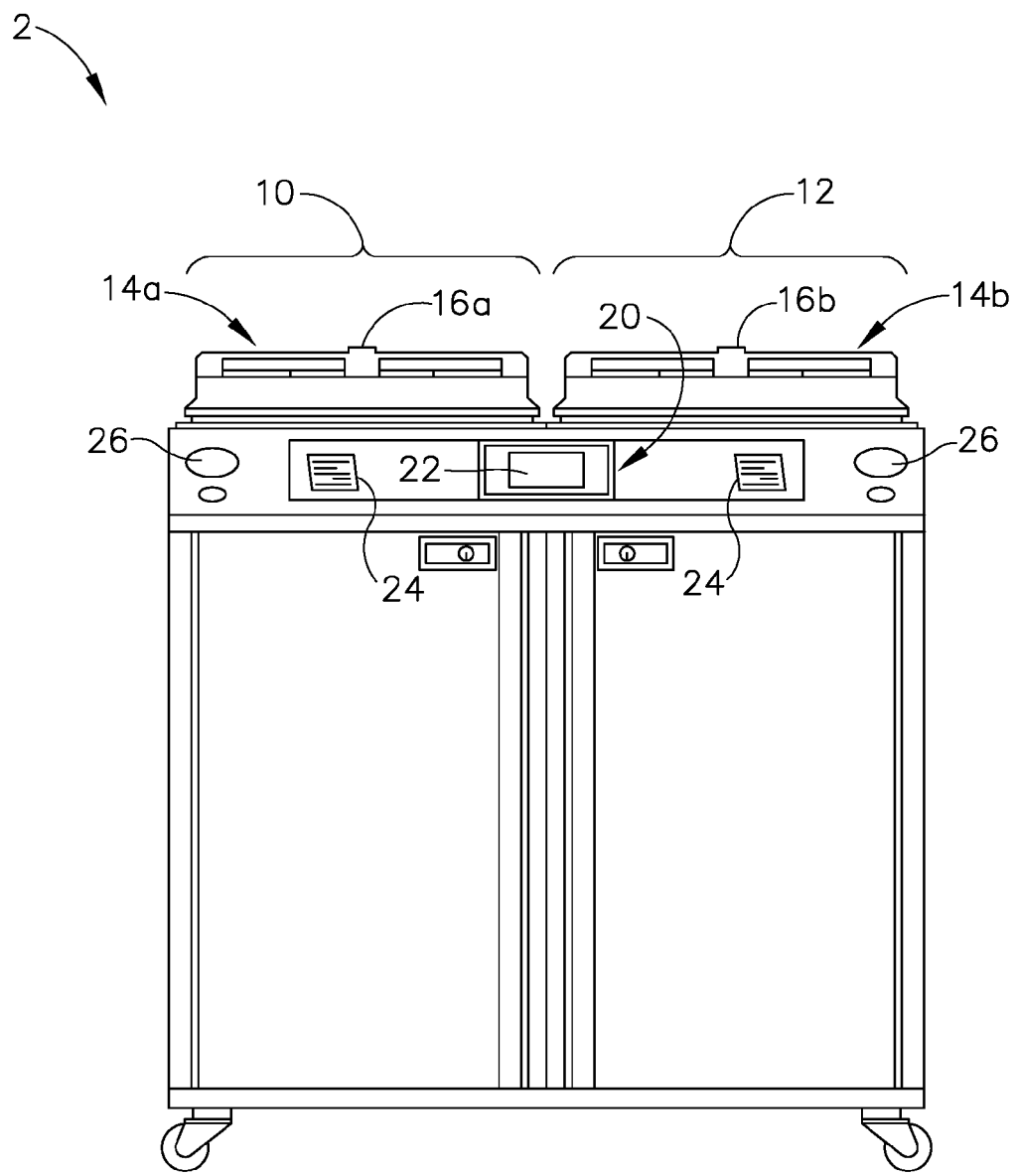
FIG. 1 depicts a front elevational view of an exemplary reprocessing system.
Figure 2:
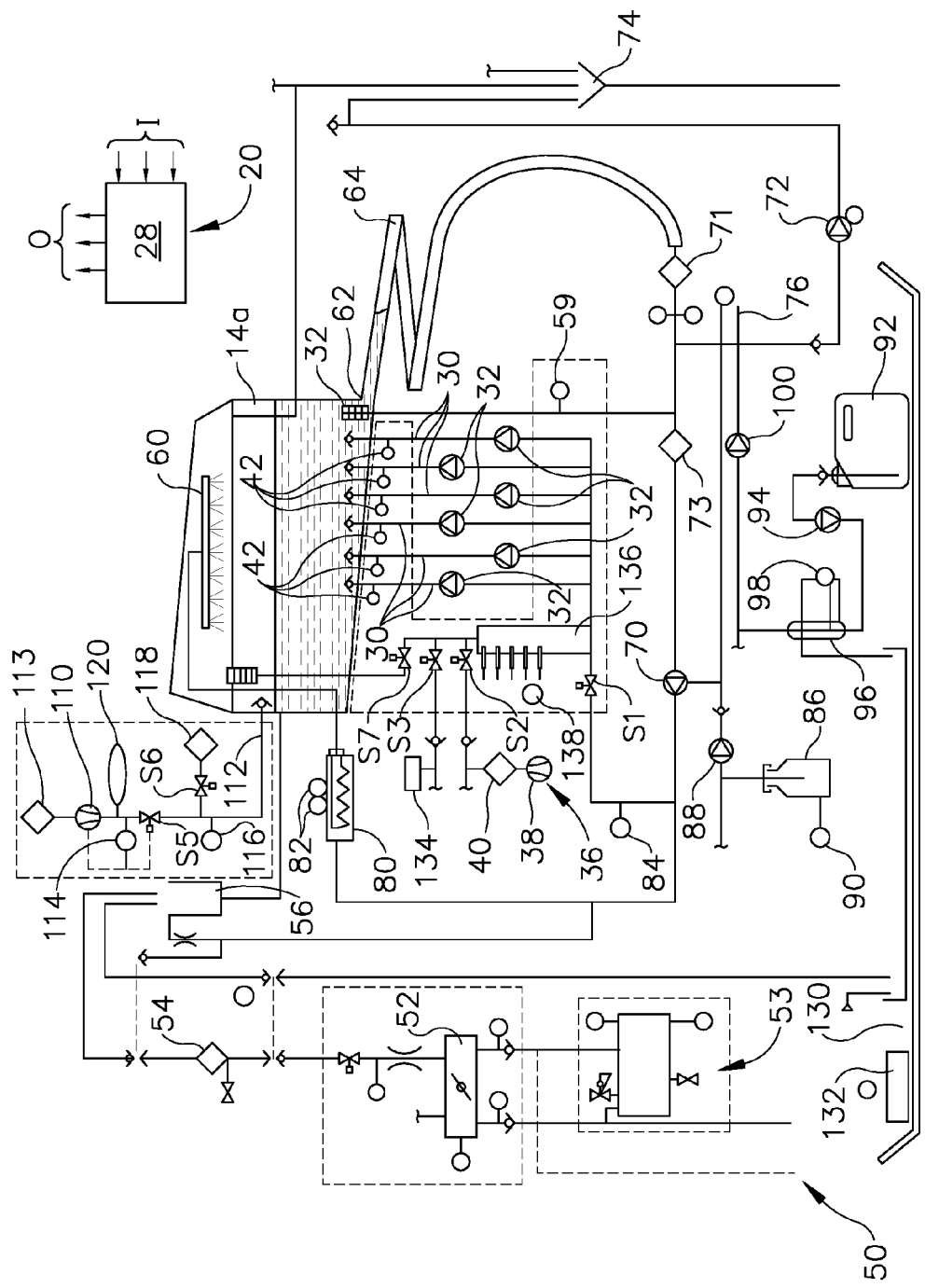
FIG. 2 depicts a schematic diagram of the reprocessing system of FIG. 1, with only a single decontamination basin shown for clarity.

FIGS. 1-2 show an exemplary reprocessing system (2) that may be used to decontaminate endoscopes and other medical devices that include channels or lumens formed therethrough. System (2) of this example generally includes a first station (10) and a second station (12). Stations (10, 12) are at least substantially similar in all respects to provide for the decontamination of two different medical devices simultaneously or in series. First and second decontamination basins (14a, 14b) receive the contaminated devices. Each basin (14a, 14b) is selectively sealed by a respective lid (16a, 16b). In the present example, lids (16a, 16b) cooperate with respective basins (14a, 14b) to provide a microbe-blocking relationship to prevent the entrance of environmental microbes into basins (14a, 14b) during decontamination operations. By way of example only, lids (16a, 16b) may include a microbe removal or HEPA air filter formed therein for venting.

A control system (20) includes one or more microcontrollers, such as a programmable logic controller (PLC), for controlling decontamination and user interface operations. Although one control system (20) is shown herein as controlling both decontamination stations (10, 12), those skilled in the art will recognize that each station (10, 12) can include a dedicated control system. A visual display (22) displays decontamination parameters and machine conditions for an operator, and at least one printer (24) prints a hard copy output of the decontamination parameters for a record to be filed or attached to the decontaminated device or its storage packaging. It should be understood that printer (24) is merely optional. In some versions, visual display (22) is combined with a touch screen input device. In addition, or in the alternative, a keypad and/or other user input feature is provided for input of decontamination process parameters and for machine control. Other visual gauges (26) such as pressure meters and the like provide digital or analog output of decontamination or medical device leak testing data.

FIG. 2 diagrammatically illustrates just one decontamination station (10) of reprocessing system (2), but those skilled in the art will recognize that decontamination station (12) may be configured and operable just like decontamination station (10). It should also be understood that reprocessing system (2) may be provided with just one single decontamination station (10, 12) or more than two decontamination stations (10, 12).

Decontamination basin (14a) receives an endoscope (200) (see FIG. 3) or other medical device therein for decontamination. Any internal channels of endoscope (200) are connected with flush conduits, such as flush lines (30). Each flush line (30) is connected to an outlet of a corresponding pump (32), such that each flush line (30) has a dedicated pump (32) in this example. Pumps (32) of the present example comprise peristaltic pumps that pump fluid, such as liquid and air, through the flush lines (30) and any internal channels of endoscope (200). Alternatively, any other suitable kind of pump(s) may be used. In the present example, pumps (32) can either draw liquid from basin (14a) through a filtered drain and a valve (S1); or draw decontaminated air from an air supply system (36) through a valve (S2). Air supply system (36) of the present example includes a pump (38) and a microbe removal air filter (40) that filters microbes from an incoming air stream.

A pressure switch or sensor (42) is in fluid communication with each flush line (30) for sensing excessive pressure in the flush line. Any excessive pressure or lack of flow sensed may be indicative of a partial or complete blockage (e.g., by bodily tissue or dried bodily fluids) in an endoscope (200) channel to which the relevant flush line (30) is connected. The isolation of each flush line (30) relative to the other flush lines (30) allows the particular blocked channel to be easily identified and isolated, depending upon which sensor (42) senses excessive pressure or lack of flow.

Basin (14a) is in fluid communication with a water source (50), such as a utility or tap water connection including hot and cold inlets, and a mixing valve (52) flowing into a break tank (56). A microbe removal filter (54), such as a 0.2 μm or smaller absolute pore size filter, decontaminates the incoming water, which is delivered into break tank (56) through the air gap to prevent backflow. A sensor (59) monitors liquid levels within basin (14a). An optional water heater (53) can be provided if an appropriate source of hot water is not available. The condition of filter (54) can be monitored by directly monitoring the flow rate of water therethrough or indirectly by monitoring the basin fill time using a float switch or the like. When the flow rate drops below a select threshold, this indicates a partially clogged filter element that requires replacement.

A basin drain (62) drains liquid from basin (14a) through an enlarged helical tube (64) into which elongated portions of endoscope (200) can be inserted. Drain (62) is in fluid communication with a recirculation pump (70) and a drain pump (72). Recirculation pump (70) recirculates liquid from basin drain (62) to a spray nozzle assembly (60), which sprays the liquid into basin (14a) and onto endoscope (200). A coarse screen (71) and a fine screen (73) filter out particles in the recirculating fluid. Drain pump (72) pumps liquid from basin drain (62) to a utility drain (74). A level sensor (76) monitors the flow of liquid from pump (72) to utility drain (74). Pumps (70, 72) can be simultaneously operated such that liquid is sprayed into basin (14a) while basin (14a) is being drained, to encourage the flow of residue out of basin (14a) and off of endoscope (200). Of course, a single pump and a valve assembly could replace dual pumps (70, 72).

An inline heater (80), with temperature sensors (82), upstream of recirculation pump (70), heats the liquid to optimum temperatures for cleaning and/or disinfection. A pressure switch or sensor (84) measures pressure downstream of circulation pump (70). In some variations, a flow sensor is used instead of pressure sensor (84), to measure fluid flow downstream of circulation pump (70). Detergent solution (86) is metered into the flow downstream of circulation pump (70) via a metering pump (88). A float switch (90) indicates the level of detergent (86) available. Disinfectant (92) is metered into the flow upstream of circulation pump (70) via a metering pump (94). To more accurately meter disinfectant (92), pump (94) fills a metering prechamber (96) under control of a fluid level switch (98) and control system (20). By way of example only, disinfection solution (92) may comprise CIDEX© Activated Glutaraldehyde Solution by Advanced Sterilization Products of Irvine, Calif. By way of further example only, disinfection solution (92) may comprise ortho-phthalaldehyde (OPA). By way of further example only, disinfection solution (92) may comprise peracetic acid (PAA).

Some endoscopes (200) include a flexible outer housing or sheath surrounding the individual tubular members and the like that form the interior channels and other parts of endoscope (200). This housing defines a closed interior space, which is isolated from patient tissues and fluids during medical procedures. It may be important that the sheath be maintained intact, without cuts or other holes that would allow contamination of the interior space beneath the sheath. Therefore, reprocessing system (2) of the present example includes means for testing the integrity of such a sheath. In particular, an air pump (e.g., pump (38) or another pump (110)) pressurizes the interior space defined by the sheath of endoscope (200) through a conduit (112) and a valve (S5). In the present example, a HEPA or other microbe-removing filter (113) removes microbes from the pressurizing air. A pressure regulator (114) prevents accidental over pressurization of the sheath. Upon full pressurization, valve (S5) is closed and a pressure sensor (116) looks for a drop in pressure in conduit (112), which would indicate the escape of air through the sheath of endoscope (200). A valve (S6) selectively vents conduit (112) and the sheath of endoscope (200) through an optional filter (118) when the testing procedure is complete. An air buffer (120) smoothes out pulsation of pressure from air pump (110).

In the present example, each station (10, 12) also contains a drip basin (130) and spill sensor (132) to alert the operator to potential leaks.

An alcohol supply (134), controlled by a valve (S3), can supply alcohol to channel pumps (32) after rinsing steps, to assist in removing water from channels (210, 212, 213, 214, 217, 218) of endoscope (200).

Flow rates in lines (30) can be monitored via channel pumps (32) and pressure sensors (42). If one of pressure sensors (42) detects too high a pressure, the associated pump (32) is deactivated. The flow rate of pump (32) and its activated duration time provide a reasonable indication of the flow rate in an associated line (30). These flow rates are monitored during the process to check for blockages in any of the channels of endoscope (200). Alternatively, the decay in the pressure from the time pump (32) cycles off can also be used to estimate the flow rate, with faster decay rates being associated with higher flow rates.

A more accurate measurement of flow rate in an individual channel may be desirable to detect subtler blockages. To that end, a metering tube (136) having a plurality of level indicating sensors (138) fluidly connects to the inputs of channel pumps (32). In some versions, a reference connection is provided at a low point in metering tube (136) and a plurality of sensors (138) are arranged vertically above the reference connection. By passing a current from the reference point through the fluid to sensors (138), it can be determined which sensors (138) are immersed and therefore determine the level within metering tube (136). In addition, or in the alternative, any other suitable components and techniques may be used to sense fluid levels. By shutting valve (S1) and opening a vent valve (S7), channel pumps (32) draw exclusively from metering tube (136). The amount of fluid being drawn can be very accurately determined based upon sensors (138). By running each channel pump (32) in isolation, the flow therethrough can be accurately determined based upon the time and the volume of fluid emptied from metering tube (136).

In addition to the input and output devices described above, all of the electrical and electromechanical devices shown are operatively connected to and controlled by control system (20). Specifically, and without limitation, switches and sensors (42, 59, 76, 84, 90, 98, 114, 116, 132 136) provide input (I) to microcontroller (28), which controls the cleaning and/or disinfection cycles and other machine operations in accordance therewith. For example, microcontroller (28) includes outputs (O) that are operatively connected to pumps (32, 38, 70, 72, 88, 94, 100, 110), valves (S1, S2, S3, S5, S6, S7), and heater (80) to control these devices for effective cleaning and/or disinfection cycles and other operations.

Figure 3:
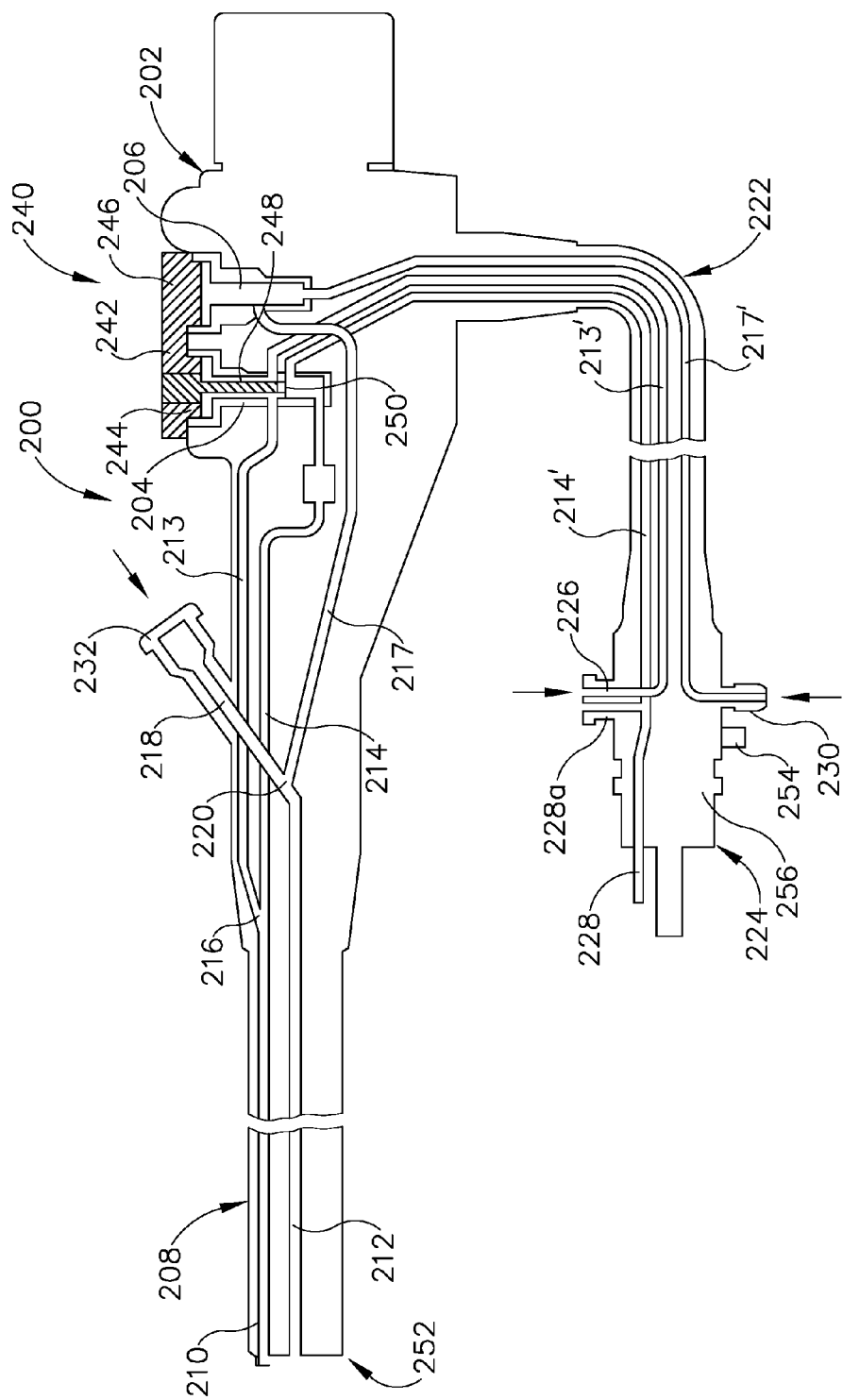
FIG. 3 depicts a cross-sectional side view of proximal and distal portions of an endoscope that may be decontaminated using the reprocessing system of FIG. 1.

As shown in FIG. 3, endoscope (200) has a head part (202). Head part (202) includes openings (204, 206) formed therein. During normal use of endoscope (200), an air/water valve (not shown) and a suction valve (not shown) are arranged in openings (204, 206). A flexible shaft (208) is attached to head part (202). A combined air/water channel (210) and a combined suction/biopsy channel (212) are accommodated in shaft (208). A separate air channel (213) and water channel (214) are also arranged in head part (202) and merge into air/water channel (210) at the location of a joining point (216). It will be appreciated that the term "joining point" as used herein refers to an intersecting junction rather than being limited to a geometrical point and, the terms may be used interchangeably. Furthermore, a separate suction channel (217) and biopsy channel (218) are accommodated in head part (202) and merge into suction/biopsy channel (212) at the location of a joining point (220).

In head part (202), air channel (213) and water channel (214) open into opening (204) for the air/water valve (not shown). Suction channel (217) opens into opening (206) for the suction valve (not shown). Furthermore, a flexible feed hose (222) connects to head part (202) and accommodates channels (213', 214', 217'), which are connected to air channel (213), water channel (214), and suction channel (217) via respective openings (204, 206). In practice, feed hose (222) may also be referred to as the light-conductor casing. The mutually connecting air channels (213, 213') will collectively be referred to below as air channel (213). The mutually connecting water channels (214, 214') will collectively be referred to below as water channel (214). The mutually connecting suction channels (217, 217') will collectively be referred to below as suction channel (217). A connection (226) for air channel (213), connections (228, 228a) for water channel (214), and a connection (230) for suction channel (217) are arranged on the end section (224) (also referred to as the light conductor connector) of flexible hose (222). When the connection (226) is in use, connection (228a) is closed off. A connection (232) for biopsy channel (218) is arranged on head part (202).

A channel separator (240) is shown inserted into openings (204, 206). Channel separator (240) comprises a body (242) and plug members (244, 246), which occlude respective openings (204, 206). A coaxial insert (248) on plug member (244) extends inwardly of opening (204) and terminates in an annular flange (250), which occludes a portion of opening (204) to separate channel (213) from channel (214). By connecting lines (30) to openings (226, 228, 228a, 230, 232), liquid for cleaning and disinfection can be flowed through endoscope channels (213, 214, 217, 218) and out of a distal tip (252) of endoscope (200) via channels (210, 212). Channel separator (240) ensures that such liquid flows all the way through endoscope (200) without leaking out of openings (204, 206); and isolates channels (213, 214) from each other so that each channel (213, 214) has its own independent flow path. One of skill in the art will appreciate that various endoscopes having differing arrangements of channels and openings may require modifications to channel separator (240) to accommodate such differences while occluding ports in head (202) and keeping channels separated from each other so that each channel can be flushed independently of the other channels. Otherwise, a blockage in one channel might merely redirect flow to a connected unblocked channel.

A leakage port (254) on end section (224) leads into an interior portion (256) of endoscope (200) and is used to check for the physical integrity thereof, namely to ensure that no leakage has formed between any of the channels and the interior (256) or from the exterior to the interior (256).

II. Exemplary Medical Device Reprocessing Method

In an exemplary use of reprocessing system (2), an operator may start by actuating a foot pedal (not shown) to open basin lid (16*a*). Each lid (16*a*, 16*b*) may have its own foot pedal. In some versions, once pressure is removed from the foot pedal, the motion of lid (16*a*, 16*b*) stops. With lid (16*a*) open, the operator inserts shaft (208) of endoscope (200) into helical circulation tube (64). End section (224) and head section (202) of endoscope (200) are situated within basin (14*a*), with feed hose (222) coiled within basin (14*a*) with as wide a diameter as possible. Next, flush lines (30) are attached to respective endoscope openings (226, 228, 228*a*, 230, 232). Air line (112) is also connected to connector (254). In some versions, flush lines (30) are color coded, and guide located on station (10) provides a reference for the color-coded connections.

Depending on the customer-selectable configuration, control system (20) may prompt the operator to enter a user code, patient ID, endoscope code, and/or specialist code. This information may be entered manually (e.g., through touch screen (22)), automatically (e.g., by using an attached barcode wand), or in any other suitable fashion. With the information entered (if required), the operator may then close lid (16*a*). In some versions, closing lid (16*a*) requires the operator to press a hardware button and a touch-screen (22) button simultaneously to provide a fail-safe mechanism for preventing the operator's hands from being caught or pinched by the closing basin lid (16*a*). If either the hardware button or software button is released while lid (16*a*) is in the process of closing, the motion of lid (16*a*) stops.

Once lid (16*a*) is closed, the operator presses a button on touch-screen (22) to begin the washing/disinfection process. At the start of the washing/disinfection process, air pump (38) is activated and pressure within the body of endoscope (200) is monitored. When pressure reaches a predetermined level (e.g., 250 mbar), pump (38) is deactivated, and the pressure is allowed to stabilize for a certain stabilization period (e.g., 6 seconds). If pressure has not reached a certain pressure (e.g., 250 mbar) in a certain time period (e.g., 45 seconds), the program is stopped and the operator is notified of a leak. If pressure drops below a threshold (e.g., less than 100 mbar) during the stabilization period, the program is stopped and the operator is notified of the condition. Once the pressure has stabilized, the pressure drop is monitored over the course of a certain duration (e.g., 60 seconds). If pressure drop is faster than a predetermined rate (e.g., more than 10 mbar within 60 seconds), the program is stopped and the operator is notified of the condition. If the pressure drop is slower than a predetermined rate (e.g., less than 10 mbar in 60 seconds), reprocessing system (2) continues with the next step. A slight positive pressure is held within the body of endoscope (200) during the rest of the process to prevent fluids from leaking in.

A second leak test checks the adequacy of connection to the various ports (226, 228, 228*a*, 230, 232) and the proper placement of channel separator (240). A quantity of water is admitted to basin (14*a*) so as to submerge the distal end of endoscope (200) in helical tube (64). Valve (S1) is closed and valve (S7) opened; and pumps (32) are run in reverse to draw a vacuum and to ultimately draw liquid into endoscope channels (210, 212). Pressure sensors (42) are monitored to make sure that the pressure in any one channel (210, 212) does not drop and/or raise by more than a predetermined amount in a given time frame. If it does, it likely indicates that one of the connections was not made correctly and air is leaking into channel (210, 212). In any event, in the presence of an unacceptable pressure drop, control system (20) will cancel the cycle and indicate a likely faulty connection, preferably with an indication of which channel (210, 212) failed.

In the event that the leak tests are passed, reprocessing system (2) continues with a pre-rinse cycle. The purpose of this step is to flush water through channels (210, 212, 213, 214, 217, 218) to remove waste material prior to washing and disinfecting endoscope (200). To initiate the pre-rinse cycle, basin (14*a*) is filled with filtered water and the water level is detected by pressure sensor (59) below basin (14*a*). The water is pumped via pumps (32) through the interior of channels (210, 212, 213, 214, 217, 218), directly to drain (74). This water is not recirculated around the exterior surfaces of endoscope 200 during this stage. As the water is being pumped through channels (210, 212, 213, 214, 217, 218), drain pump (72) is activated to ensure that basin (14*a*) is also emptied. Drain pump (72) will be turned off when drain switch (76) detects that the drain process is complete. During the draining process, sterile air is blown via air pump (38) through all endoscope channels (210, 212, 213, 214, 217, 218) simultaneously, to minimize potential carryover.

Once the pre-rinse cycle is complete, reprocessing system (2) continues with a wash cycle. To begin the wash cycle, basin (14*a*) is filled with warm water (e.g., approximately 35° C.). Water temperature is controlled by controlling the mix of heated and unheated water. The water level is detected by pressure sensor (59). Reprocessing system (2) then adds enzymatic detergent to the water circulating in reprocessing system (2) by means of peristaltic metering pump (88). The volume is controlled by controlling the delivery time, pump speed, and inner diameter of the tubing of pump (88). Detergent solution (86) is actively pumped throughout the internal endoscope channels (210, 212, 213, 214, 217, 218) and over the outer surface of endoscope (200) for a predetermined time period (e.g., from one to five minutes, or more particularly about three minutes), by channel pumps (32) and external circulation pump (70). Inline heater (80) keeps the temperature at a predetermined temperature (e.g., approximately about 35° C.).

After detergent solution (86) has been circulating for a certain period of time (e.g., a couple of minutes), the flow rate through channels (210, 212, 213, 214, 217, 218) is measured. If the flow rate through any channel (210, 212, 213, 214, 217, 218) is less than a predetermined rate for that channel (210, 212, 213, 214, 217, 218), the channel (210, 212, 213, 214, 217, 218) is identified as blocked, the program is stopped, and the operator is notified of the condition. Peristaltic pumps (32) are run at their predetermined flow rates and cycle off in the presence of unacceptably high pressure readings at the associated pressure sensor (42). If a channel (210, 212, 213, 214, 217, 218) is blocked, the predetermined flow rate will trigger pressure sensor (42), indicating the inability to adequately pass this flow rate. As pumps (32) are peristaltic in the present example, their operating flow rate combined with the percentage of time they are cycled off due to pressure will provide the actual flow rate. The flow rate can also be estimated based upon the decay of the pressure from the time pump (32) cycles off.

At the end of the wash cycle, drain pump (72) is activated to remove detergent solution (86) from basin (14a) and channels (210, 212, 213, 214, 217, 218). Drain pump (72) turns off when drain level sensor (76) indicates that drainage is complete. During the drain process, sterile air is blown through all channels (210, 212, 213, 214, 217, 218) of endoscope (200) simultaneously to minimize potential carryover.

After the wash cycle is complete, reprocessing system (2) begins a rinse cycle. To initiate this rinse cycle, basin (14a) is again filled with warm water (e.g., at approximately 35° C.). Water temperature is controlled by controlling the mix of heated and unheated water. The water level is detected by pressure sensor (59). The rinse water is circulated within channels (210, 212, 213, 214, 217, 218) of endoscope (200) via channel pumps (32); and over the exterior of endoscope (200) via circulation pump (70) and sprinkler arm (60) for a certain period of time (e.g., one minute). As rinse water is pumped through channels (210, 212, 213, 214, 217, 218), the flow rate through channels (210, 212, 213, 214, 217, 218) is measured and if it falls below the predetermined rate for any given channel (210, 212, 213, 214, 217, 218), that channel (210, 212, 213, 214, 217, 218) is identified as blocked, the program is stopped, and the operator is notified of the condition.

At the end of the rinse cycle, drain pump (72) is activated to remove the rinse water from basin (14a) and channels (210, 212, 213, 214, 217, 218). Drain pump (72) turns off when drain level sensor (76) indicates that drainage is complete. During the drain process, sterile air is blown through all channels (210, 212, 213, 214, 217, 218) of endoscope (200) simultaneously to minimize potential carryover. In some versions, the above-described rinsing and draining cycles are repeated at least once again, to ensure maximum rinsing of detergent solution (86) from the surfaces of endoscope (200) and basin (14a).

After reprocessing system (2) has completed the desired number of rinsing and drying cycles, reprocessing system (2) proceeds to a disinfection cycle. To initiate the disinfection cycle, basin (14a) is filled with very warm water (e.g., at approximately 53° C.). Water temperature is controlled by controlling the mix of heated and unheated water. The water level is detected by pressure sensor (59). During the filling process, channel pumps (32) are off in order to ensure that the disinfection solution (92) in basin (14a) is at the in-use concentration prior to circulating through channels (210, 212, 213, 214, 217, 218) of endoscope (200).

Next, a measured volume of disinfection solution (92) is drawn from disinfectant metering pre-chamber (96) and delivered into the water in basin (14a) via metering pump (100). The volume of disinfection solution (92) is controlled by the positioning of fill level switch (98) relative to the bottom of metering pre-chamber (96). Metering pre-chamber (96) is filled until fill level switch (98) detects liquid. Disinfection solution (92) is drawn from metering pre-chamber (96) until the level of disinfection solution (92) in metering pre-chamber (96) is just below the tip of metering pre-chamber (96). After the necessary volume is dispensed, metering pre-chamber (96) is refilled from the bottle of disinfection solution (92). Disinfection solution (92) is not added until basin (14a) is filled, so that in case of a water supply problem, concentrated disinfectant is not left on endoscope (200) with no water to rinse it. While disinfection solution (92) is being added, channel pumps (32) are off in order to ensure that disinfection solution (92) in basin (14a) is at the desired in-use concentration prior to circulating through channels (210, 212, 213, 214, 217, 218) of endoscope (200).

The in-use disinfectant solution (92) is actively pumped throughout internal channels (210, 212, 213, 214, 217, 218) by pumps (32) and over the outer surface of endoscope (200) by circulation pump (70). This may be done for any suitable duration (e.g., at least 5 minutes). The temperature of the disinfection solution (92) may be controlled by in-line heater (80) to stay at a consistent temperature (e.g., about 52.5° C.). During the disinfection process, flow through each channel (210, 212, 213, 214, 217, 218) of endoscope (200) is verified by timing the delivering a measured quantity of solution through channel (210, 212, 213, 214, 217, 218). Valve (S1) is closed, and valve (S7) opened, and in turn each channel pump (32) delivers a predetermined volume to its associated channel (210, 212, 213, 214, 217, 218) from metering tube (136). This volume and the time it takes to deliver the volume, provides a very accurate flow rate through the channel (210, 212, 213, 214, 217, 218). Anomalies in the flow rate from what is expected for a channel (210, 212, 213, 214, 217, 218) of that diameter and length are flagged by control system (20) and the process stopped. As in-use disinfection solution (92) is pumped through channels (210, 212, 213, 214, 217, 218), the flow rate through channels (210, 212, 213, 214, 217, 218) is also measured as described above.

At the end of the disinfection cycle, drain pump (72) is activated to remove disinfection solution (92) solution from basin (14a) and channels (210, 212, 213, 214, 217, 218). During the draining process, sterile air is blown through all channels (210, 212, 213, 214, 217, 218) of endoscope (200) simultaneously to minimize potential carryover. As will be described in greater detail below, in some versions, the used disinfection solution (92) is tested to determine whether the concentration level is within an acceptable range or if the used disinfection solution (92) has been diluted to a point where the used disinfection solution (92) is below a certain concentration threshold. If the used disinfection solution (92) has acceptable concentration level, the used disinfection solution (92) may be used again in subsequent disinfection cycles. If the used disinfection solution (92) has a concentration below the threshold, the used disinfection solution (92) may be disposed of (e.g., via drain (74)).

After disinfection solution (92) has been drained from basin (14a), reprocessing system (2) begins a final rinse cycle. To initiate this cycle, basin (14a) is filled with sterile warm water (e.g., at approximately 45° C.) that has been passed through a filter (e.g., a 0.2 μm filter). The rinse water is circulated within channels (210, 212, 213, 214, 217, 218) by pumps (32); and over the exterior of endoscope (200) via circulation pump (70) and sprinkler arm 60) for a suitable duration (e.g., 1 minute). As rinse water is pumped through channels (210, 212, 213, 214, 217, 218), the flow rate through channels (210, 212, 213, 214, 217, 218) is measured as described above. Drain pump (72) is activated to remove the rinse water from basin (14a) and channels (210, 212, 213, 214, 217, 218). During the draining process, sterile air is blown through all channels (210, 212, 213, 214, 217, 218)

of endoscope (200) simultaneously to minimize potential carryover. In some versions, the above-described rinsing and draining cycles are repeated at least two more times, to ensure maximum rinsing of disinfection solution (92) residuals from the surfaces of endoscope (200) and basin (14a).

After the final rinse cycle is complete, reprocessing system (2) begins a final leak test. In particular, reprocessing system (2) pressurizes the body of endoscope (200) and measures the leak rate as described above. If the final leak test is successful, reprocessing system (2) indicates the successful completion of the cycles via touch-screen (22). From the time of program completion to the time at which lid (16a) is opened, pressure within the body of endoscope (200) is normalized to atmospheric pressure by opening vent valve (S5) at a predetermined rate (e.g., valve (S5) opened for 10 seconds every minute).

Depending on customer-selected configuration, reprocessing system (2) may prevent lid (16a) from being opened until a valid user identification code is entered. Information about the completed program, including the user ID, endoscope ID, specialist ID, and patient ID are stored along with the sensor data obtained throughout the program. If a printer is connected to reprocessing system (2), and if requested by the operator, a record of the disinfection program will be printed. Once a valid user identification code has been entered, lid (16a) may be opened (e.g., using the foot pedal as described above). Endoscope (200) is then disconnected from flush lines (30) and removed from basin (14a). Lid (16a) can then be closed using both the hardware and software buttons as described above.

III. Exemplary Repossessing System with Actuating Panel Assembly

In some instances, when an operator is loading a contaminated endoscope (200) into reprocessing system (2), a portion of reprocessing system (2) external to decontamination basins (14a, 14b) may have unwanted contact with contaminated endoscope (200), thereby contaminating external portions of reprocessing system (2). For instance, flexible shaft (208) may have a length making it difficult for an operator to prevent unwanted contact between contaminated endoscope (200) and a front portion of reprocessing system (2), such as visual display (22). Thus, once a contaminated portion of flexible shaft (208) comes into contact with a front portion of reprocessing system (2), the contacted region of reprocessing system (2) will become contaminated.

After endoscope (200) is reprocessed in reprocessing system (2), endoscope (200) may be removed from reprocessing system (2) as described above. However, if contaminated portions of reprocessing system (2) external to decontamination basins (14a, 14b) had previously come into contact with a contaminated endoscope (200) and have not been subsequently sanitized, accidental contact between a reprocessed endoscope (200) and contaminated external portions of reprocessing system (2) may cross-contaminate endoscope (200). Therefore, it may be desirable to provide a feature designed to prevent cross-contamination between endoscope (200) and reprocessing system (2) when removing a processed endoscope (200) from reprocessing system (2).

Figure 4:
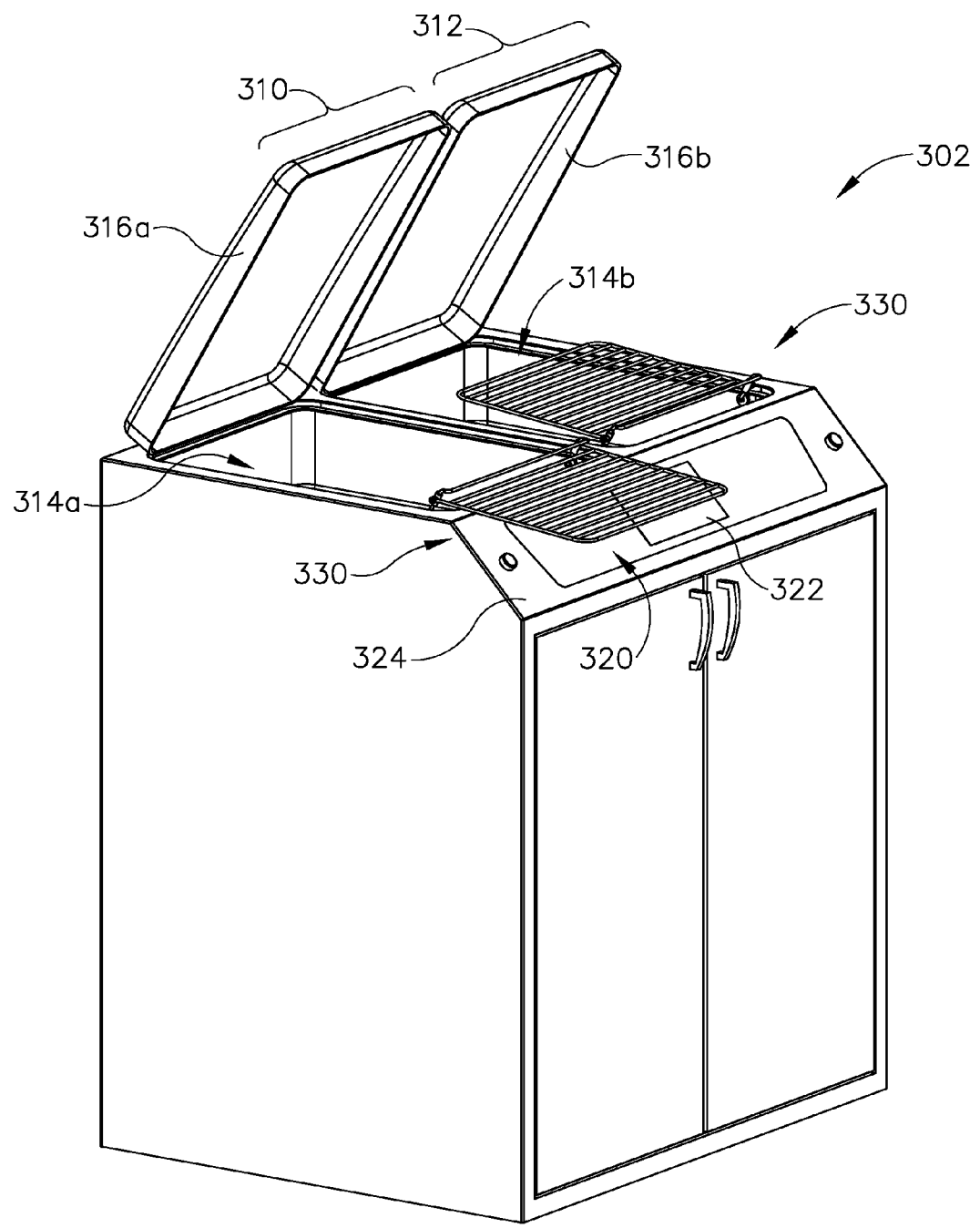
FIG. 4 depicts a perspective view of another exemplary reprocessing system that may be used as an alternative to the reprocessing system of FIG. 1.

FIG. 4 shows an alternative reprocessing system (302) that may be used as an alternative to reprocessing system (2) described above. It should be understood that reprocessing system (302) is substantially similar to reprocessing system (20) described above, with differences elaborated below. Therefore, methods of using reprocessing system (302) may be substantially similar to those described above, with differences elaborated below. Moreover, reprocessing system (302) may have the same components and functionality as reprocessing system (2), except as otherwise indicated below. As will be described in greater detail below, reprocessing system (302) includes an actuating panel assembly (330) that is designed to move from within a decontamination basin (314a, 314b) to partially extend outwardly from decontamination basin (314a, 314b). Actuating panel assembly (330) may help prevent cross-contamination between a reprocessed endoscope (200) and external surfaces of reprocessing system (302).

Reprocessing system (302) includes a first station (310), a second station (312), and a control system (320), which are substantially similar to first station (10), second station (12), and control system (20) described above respectively, with differences described below. Control system (320) includes a visual display (322) which may be substantially similar to visual display (22) described above. Control system (320) also includes a front dashboard (324) on which visual display (322) is mounted. While in the current example, control system (320) is physically attached to first station (310) and second station (312), control system (320) may be located at any other suitable location that would be apparent to one having ordinary skill in the art in view of the teachings herein. For example, control system (320) may be attached to a cable harness any suitable distance away from first station (310) and second station (312), or located at a remote location in wireless communication with the rest of reprocessing system (302). Front dashboard (324) is directly adjacent to first station (310) and second station (312). An operator may place endoscope (200) above front dashboard (324) when loading and unloading endoscope (200). Therefore, dashboard (324), and other external portions of reprocessing system (302) adjacent to dashboard (324), may be at risk for contamination. In particular, dashboard (324) and adjacent surfaces may inadvertently come into contact with flexible shaft (208) as the operator loads a contaminated endoscope (200) into a selected one of stations (310, 312).

First station (310) includes decontamination basin (314a) and lid (316a), which are substantially similar to decontamination basin (14a) and lid (16a) described above, with differences described below. Similarly, second station (312) includes decontamination basin (314b) and lid (316a), which are substantially similar to decontamination basin (14b) and lid (16b) described above, with differences described below. Both stations (310, 312) also include actuating panel assembly (330).

In FIG. 4, second station (312) has actuating panel assembly (330) in a withdrawn position. While actuating panel assembly (330) is in the withdrawn position, lid (316b) may close, thereby enclosing actuating panel assembly (330) within lid (316b) and decontamination basin (314b). It should be understood that actuating panel assembly (330) is located within decontamination basin (314b) such that endoscope (200) may also fit within decontamination basin (314b) beneath actuating panel assembly (330). An operator may then run a reprocessing cycle, similar to that described above, in order to decontaminate endoscope (200). It should be understood that the reprocessing cycle will also decontaminate actuating panel assembly (330).

Also in FIG. 4, first station (310) has actuating panel assembly (330) in an extended position. While actuating panel assembly (330) is in the extended position, lid (316a) may not fully close. However, endoscope (200) may be loaded and unloaded from decontamination basin (314a) while actuating panel assembly (330) is in the extended position. As will be described below, actuating panel assembly (330) in the extended position may help prevent cross-contamination between endoscope (200) and an exterior of reprocessing system (302). Additionally, as will be described in greater detail below, actuation panel assembly (330) may be configured to selectively latch from the withdrawn position to the extended position such that actuation panel assembly (330) is self-supported in both positions.

Figure 5:
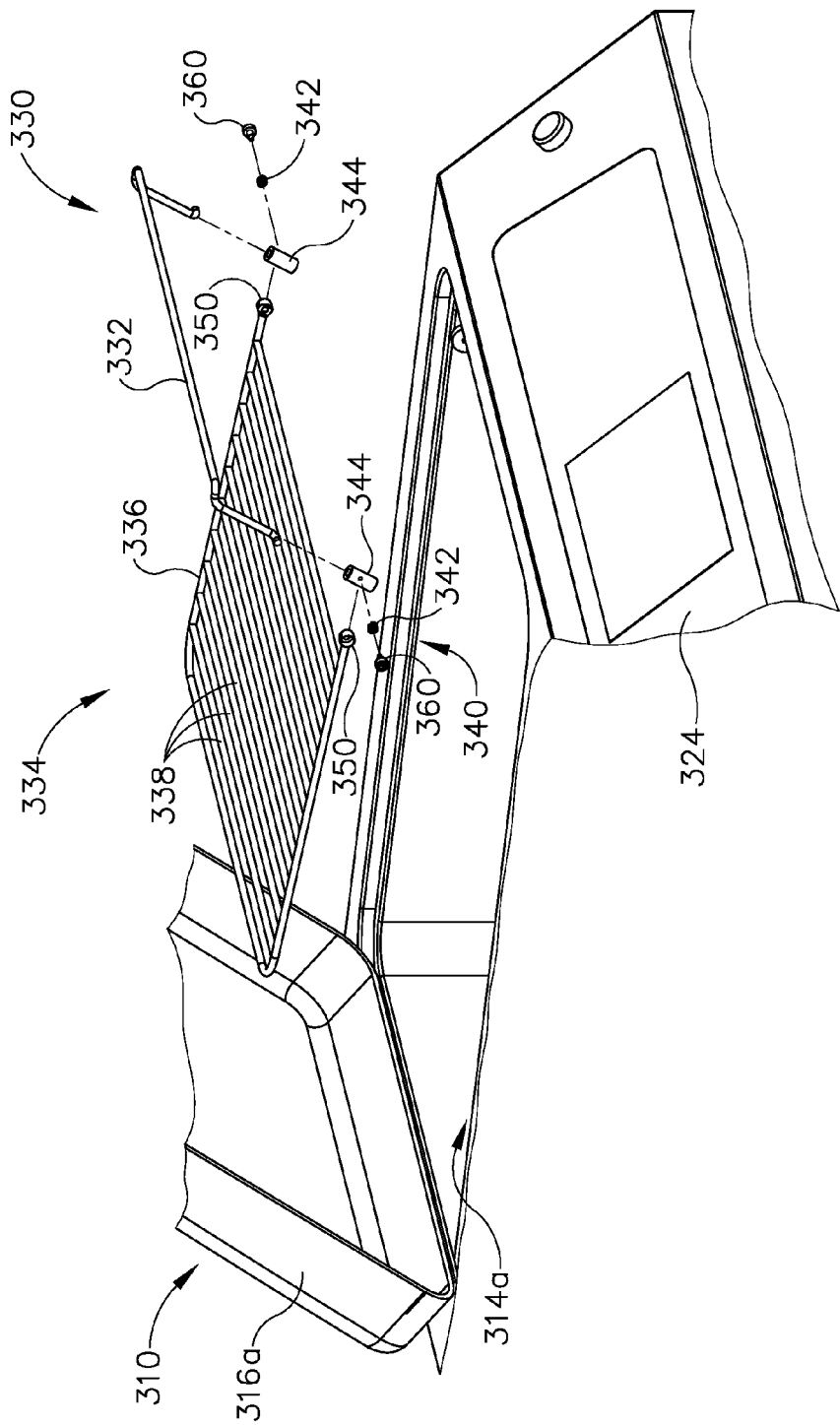
FIG. 5 depicts an exploded perspective view of an actuating panel assembly of the reprocessing system of FIG. 4.

FIG. 5 shows an exploded view of actuating assembly (300) above decontamination basin (314a). It should be understood that while actuating assembly (300) is being described within decontamination basin (314a) of first station (310), actuating assembly (300) within decontamination basin (314b) of second station (312) may be substantially similar. Actuating panel assembly (330) includes a rail (332), a panel (334), and a pair of latching assemblies (340) associated with opposite ends of rail (332). Ends of rail (332) are fixed to the interior walls of decontamination basin (314a). Therefore, rail (332) is not intended to actuate relative to basin (314) when actuating panel assembly (330) moves from the withdrawn position to the extended position or vice versa. While in the current example one rail (332) is unitarily connected to opposite ends of decontamination basin (314a), any other suitable number of rails (332) may be used as would be apparent to one having ordinary skill in the art. For example, two individual rails (332) may be fixed on opposite ends of decontamination basin (314a). Alternatively, three individual rails (332) may be utilized, where two rails (332) are fixed on opposite ends of decontamination basin (314a) while third rail (332) is a hollow tube configured to freely spin and/or slide on both of fixed rails (332). Third rail (332) may be perforated with holes to improve fluid communication and improve spinning and/or sliding if surfaces of third rail (332) come into contact with flexible shaft (208) as an operator loads a contaminated endoscope (200) into a selected one of stations (310, 312).

Figure 10:
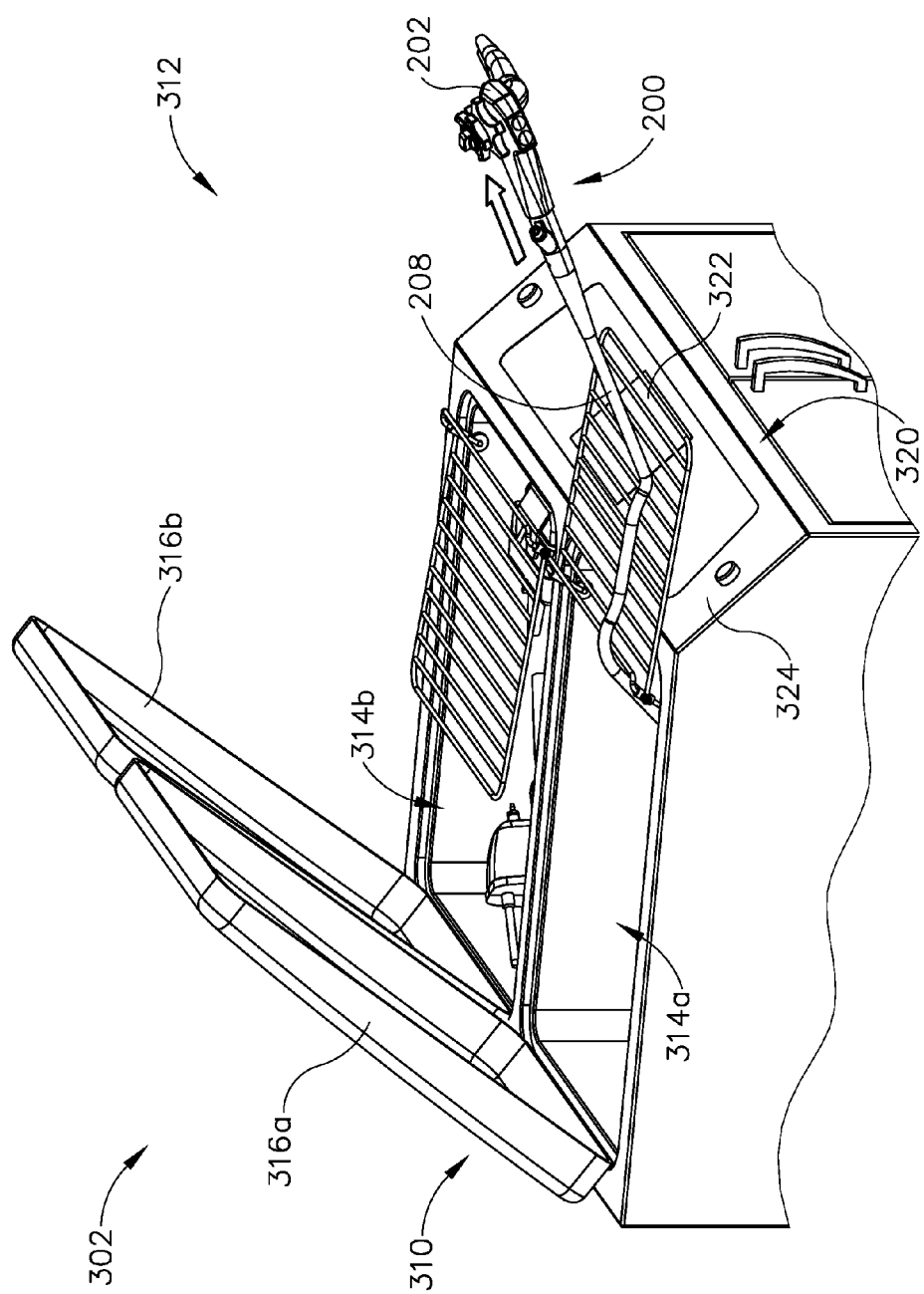
FIG. 10 depicts a perspective view of the reprocessing system of FIG. 4, with the first and second lids in an open configuration, with the first actuating panel assembly in a fully open configuration, and with a second actuating panel assembly in the closed configuration, where a recently sterilized endoscope of FIG. 3 is being removed such that a flexible portion of the endoscope rests against the first actuating panel assembly.
Figure 11A:
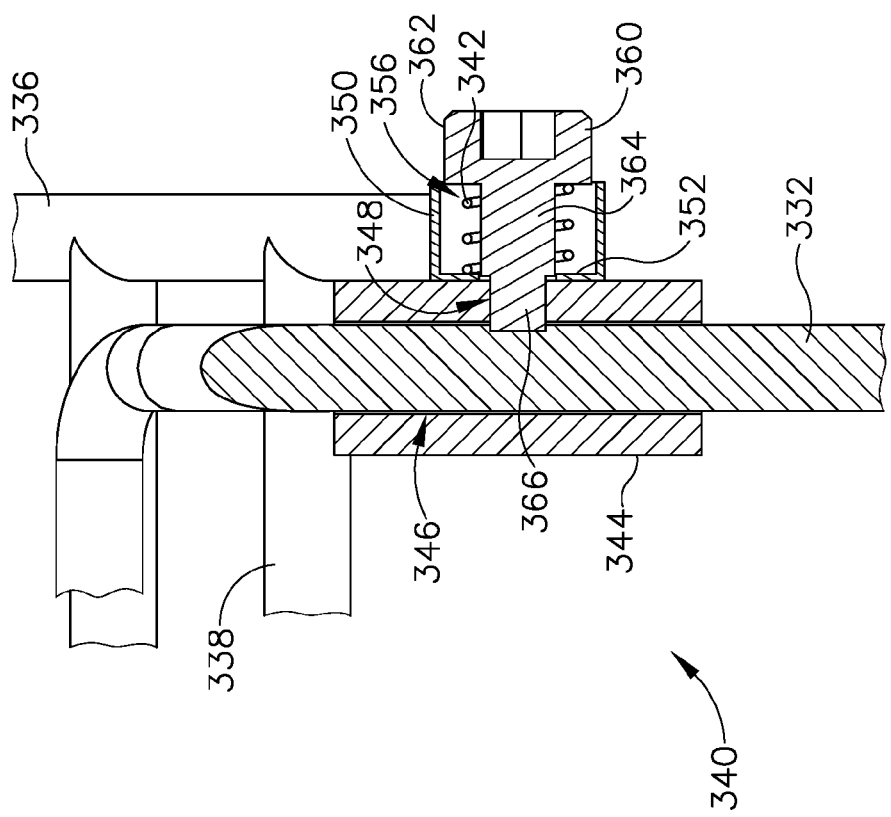
FIG. 11A depicts a cross-sectional view, taken along line 11-11 of FIG. 7, where the actuating panel assembly of FIG. 5 is in the closed configuration.
Figure 11B:
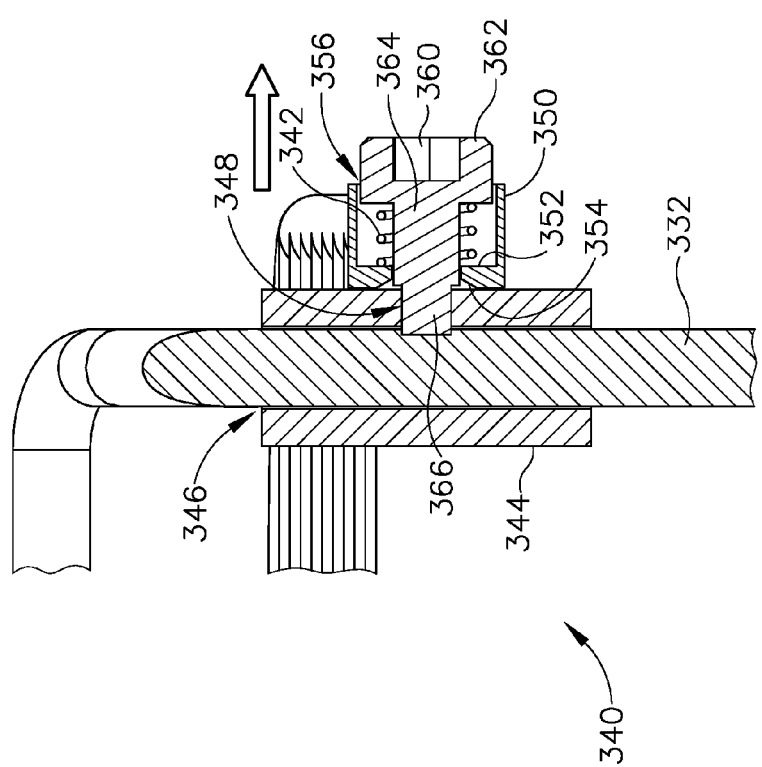
FIG. 11B depicts a cross-sectional view, taken along line 11-11 of FIG. 7, where the actuating panel assembly of FIG. 5 is in the partially open configuration.
Figure 11C:
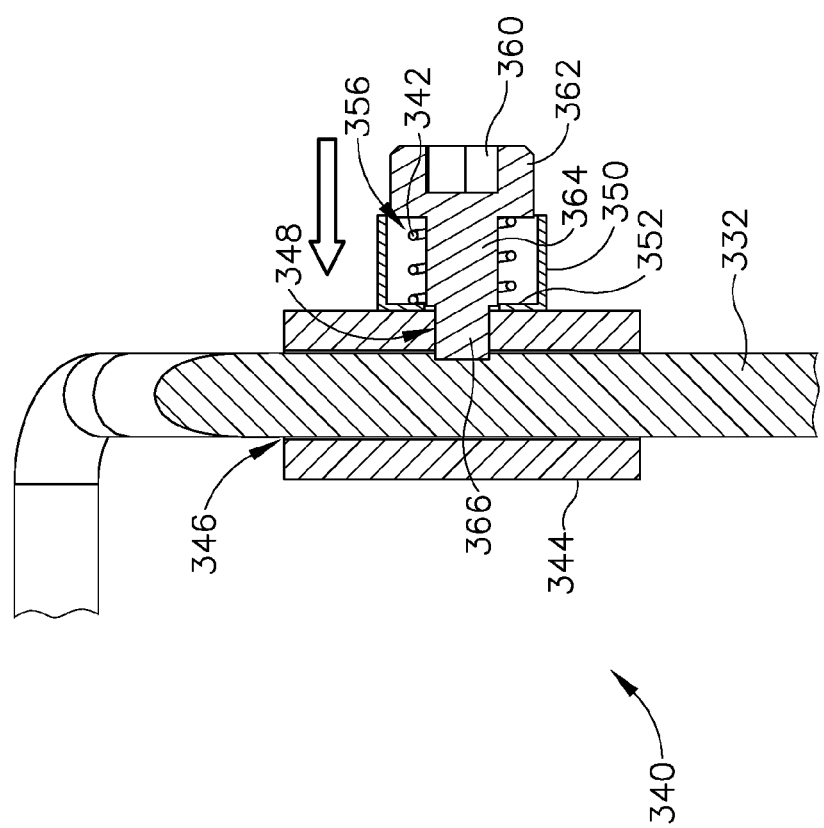
FIG. 11C depicts a cross-sectional view, taken along line 11-11 of FIG. 7, where the actuating panel assembly of FIG. 5 is in the open configuration.

Panel (334) is pivotally coupled to rail (332) via latching assembly (340). Panel (334) includes a peripheral frame (336) with a plurality of lateral bars (338) extending within peripheral frame (336). Lateral bars (338) cooperate with peripheral frame (336) to provide a grate configuration. Lateral bars (338) are spaced from one another in order to allow fluid communication from an upper side of panel (334) to a lower side of panel (334) when actuating panel assembly (330) is in the withdrawn position and lid (116a, 116b) is closed. Enhancing fluid communication between the upper side and lower side of panel (334) may help ensure panel (334) is thoroughly sanitized during the reprocessing method. Additionally, lateral bars (338) are dimensioned and spaced in order to provide support for endoscope (200) while being removed such that endoscope (200) does not touch any exterior portion of reprocessing system (302), as can be seen in FIG. 10. While in the current example lateral bars (338) extend across peripheral frame (336) laterally, any other suitable orientation may be used as would be apparent to one have ordinary skill in the art in view of the teachings herein. Additionally, while in the current example bars (338) are used to provide fluid communication and structure support as described above, any other suitable geometry may be used as would be apparent to one having ordinary skill in the art in view of the teachings herein.

Figure 6:
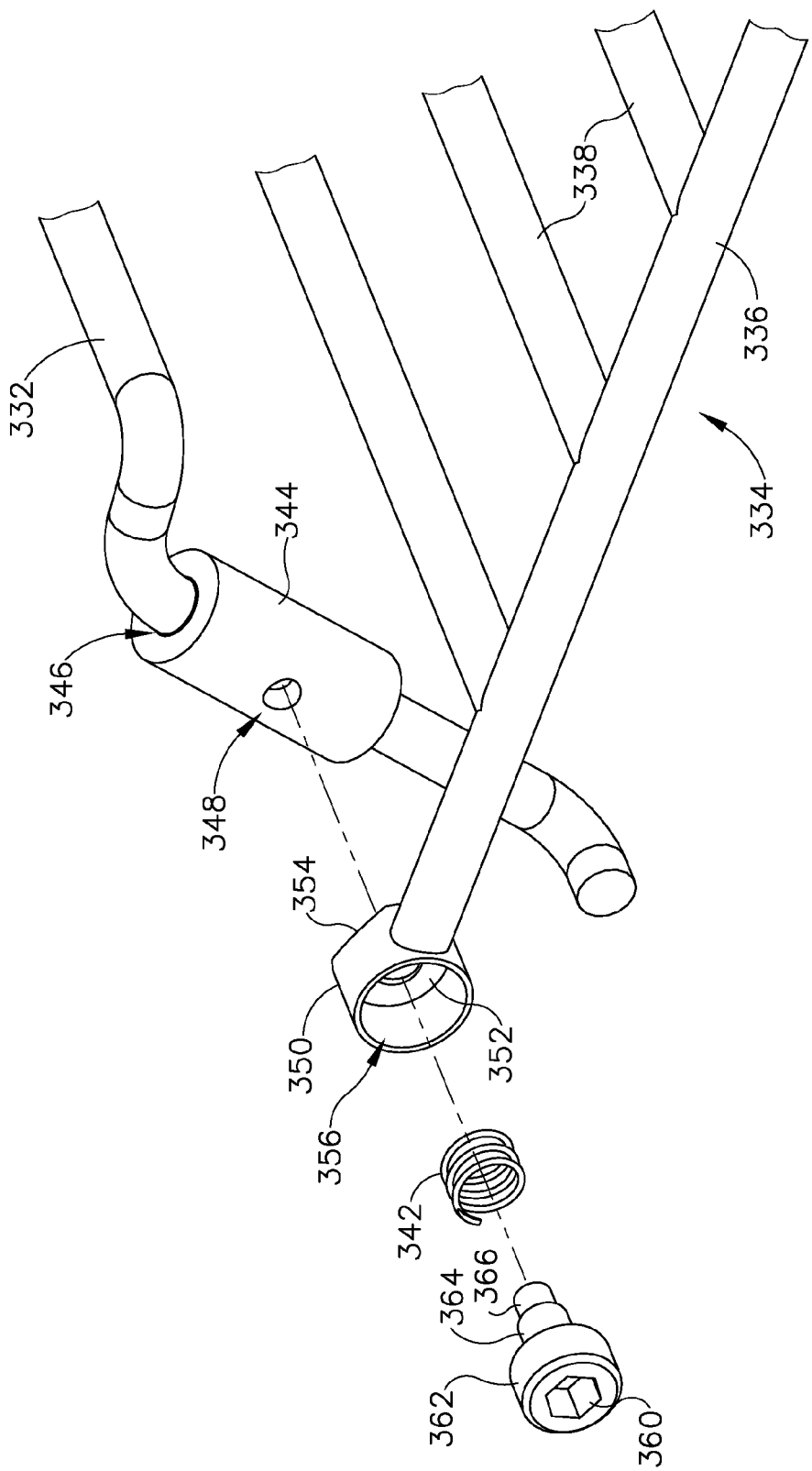
FIG. 6 depicts an exploded perspective view of a latching assembly of the actuating panel assembly of FIG. 5.
Figure 7:
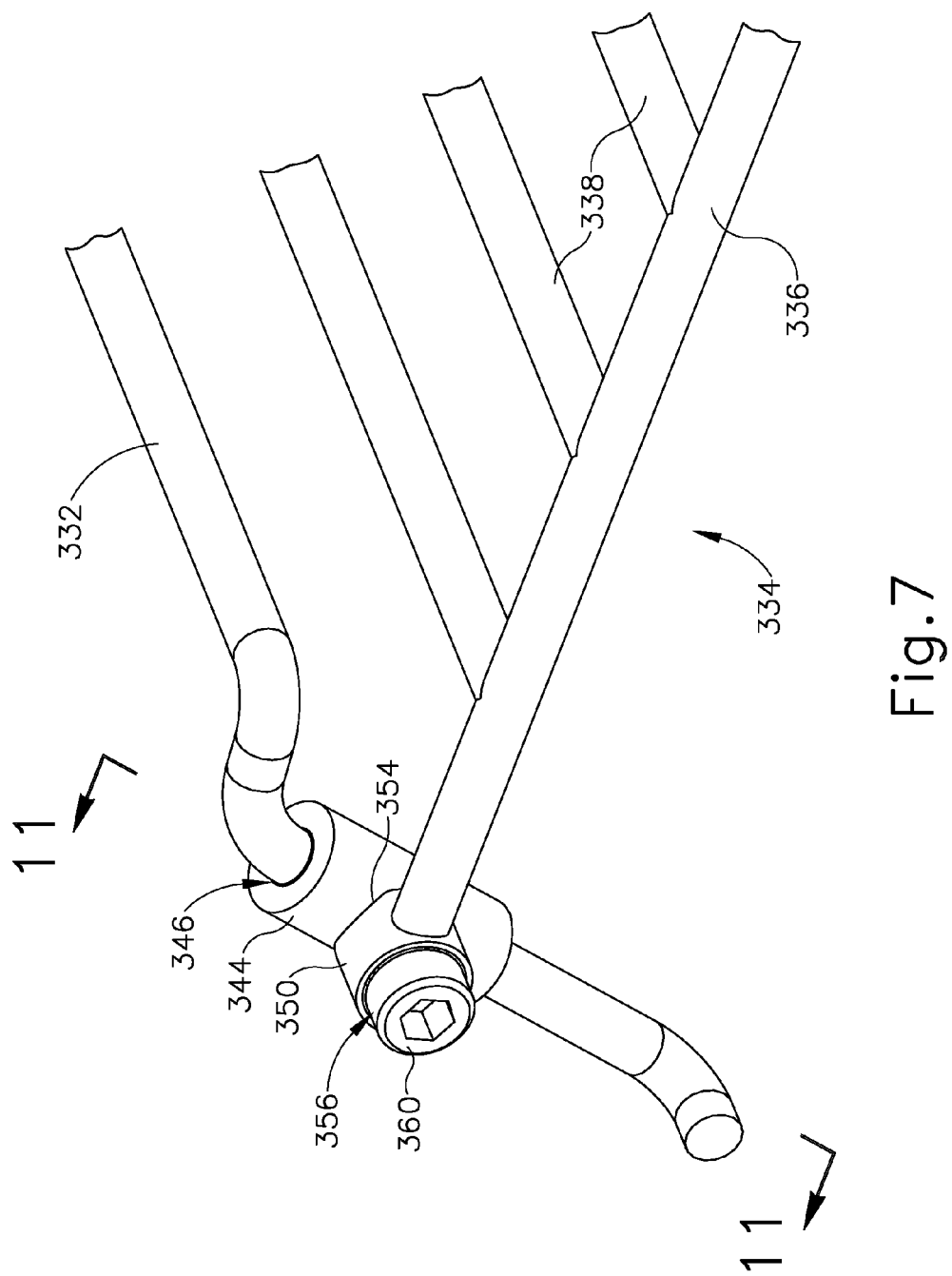
FIG. 7 depicts a perspective view of the latching assembly of FIG. 6.
Figure 8:
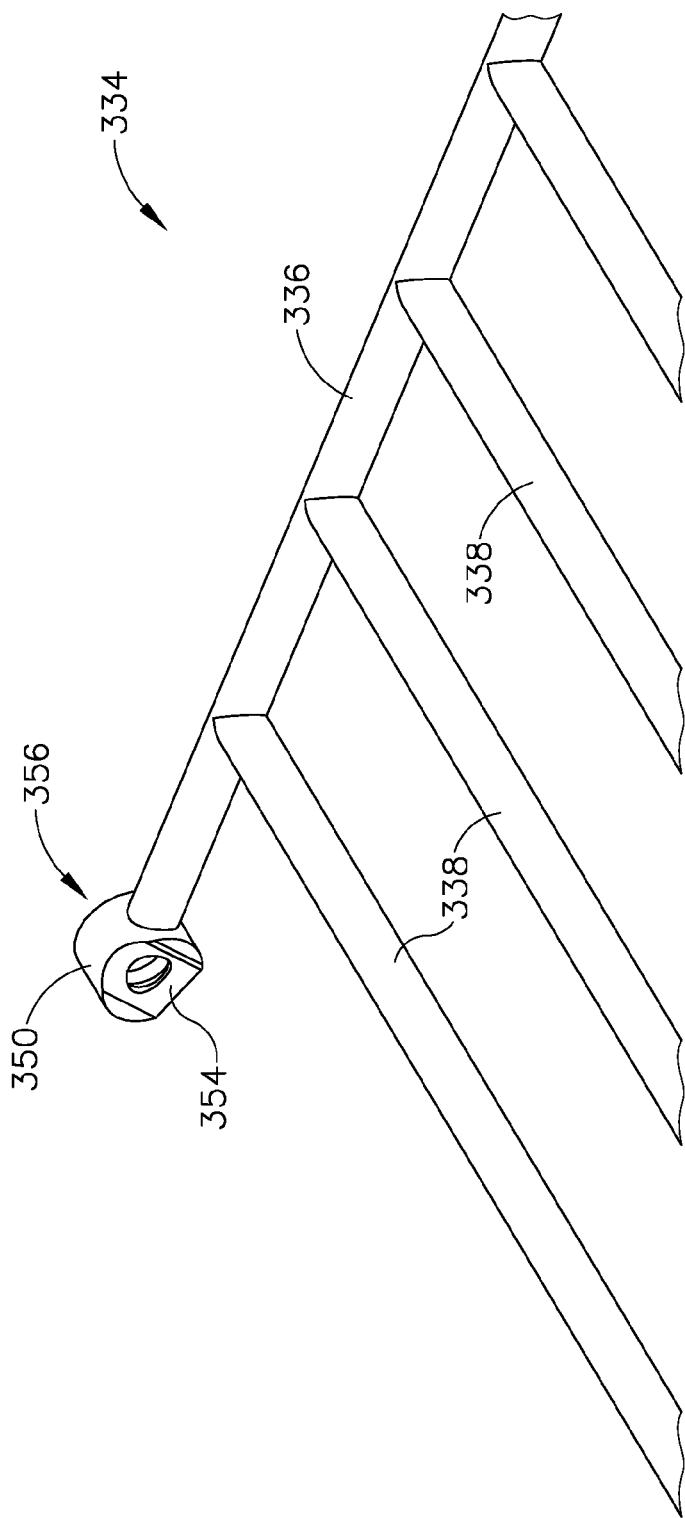
FIG. 8 depicts a perspective view of a panel of the actuating panel assembly of FIG. 5.
Figure 9A:
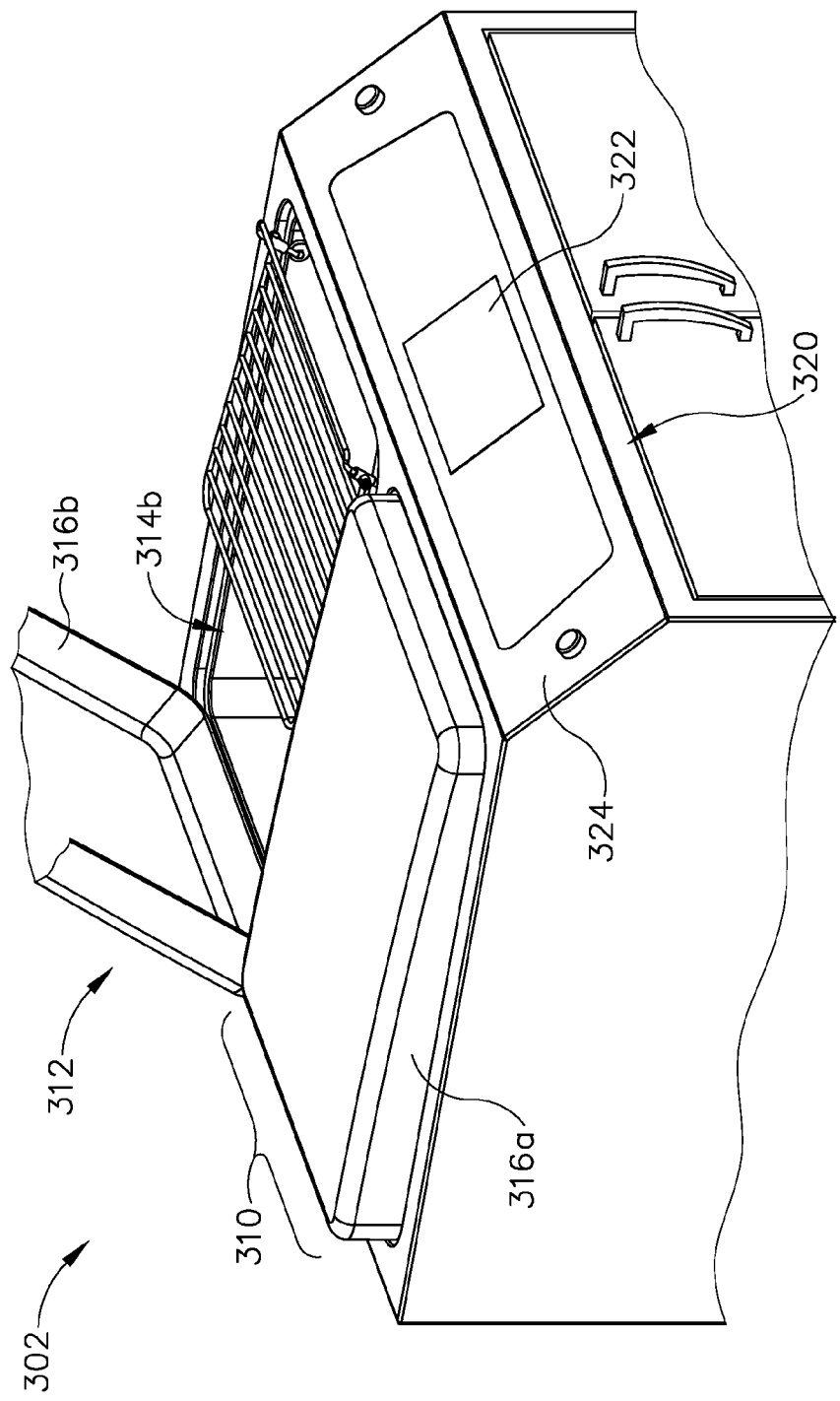
FIG. 9A depicts a perspective view of the reprocessing system of FIG. 4, with a first lid in a closed configuration and a second lid in an open configuration.
Figure 9B:
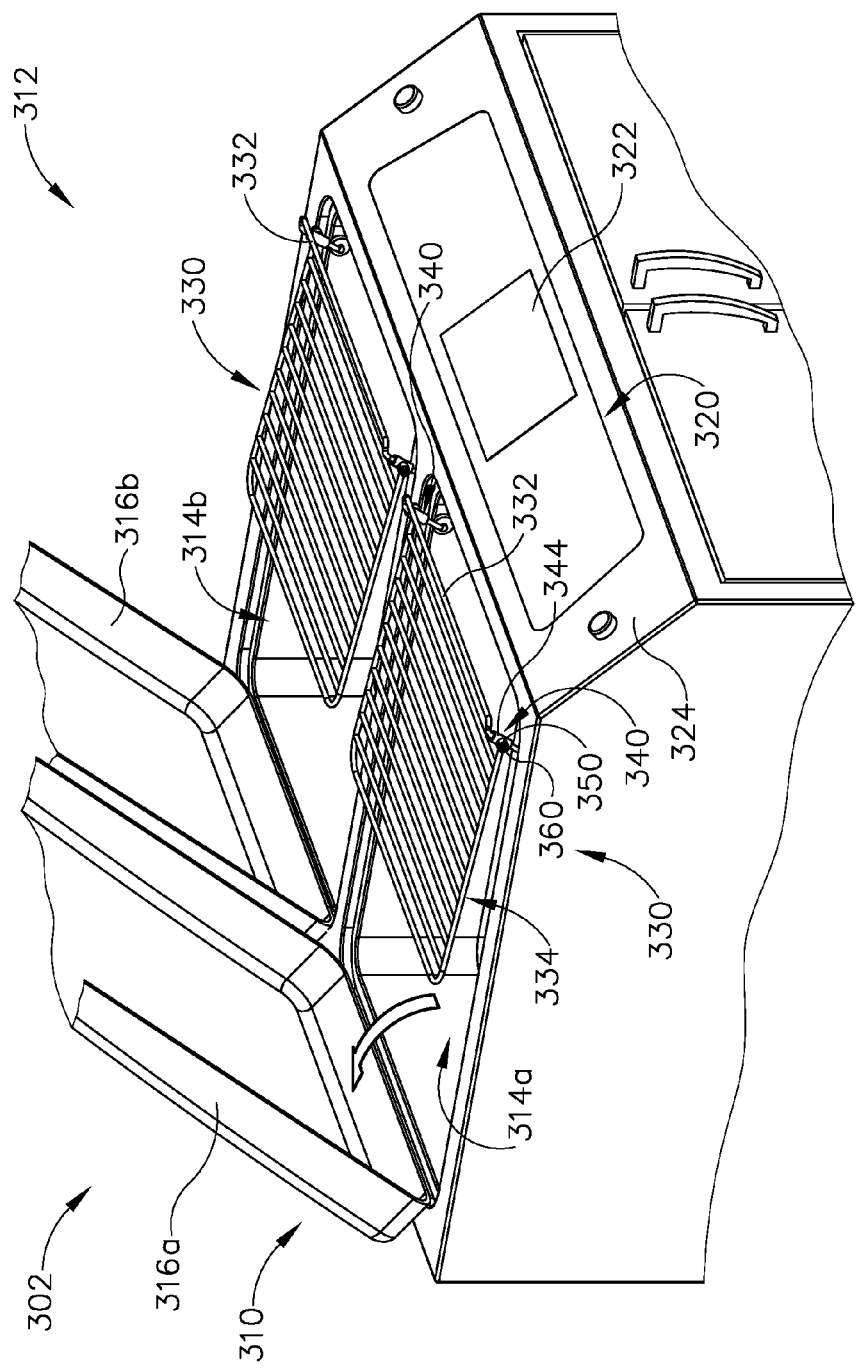
FIG. 9B depicts a perspective view of the reprocessing system of FIG. 4, with the first and second lids in an open configuration, and with the actuating panel assemblies of FIG. 5 in a closed configuration.
Figure 9C:
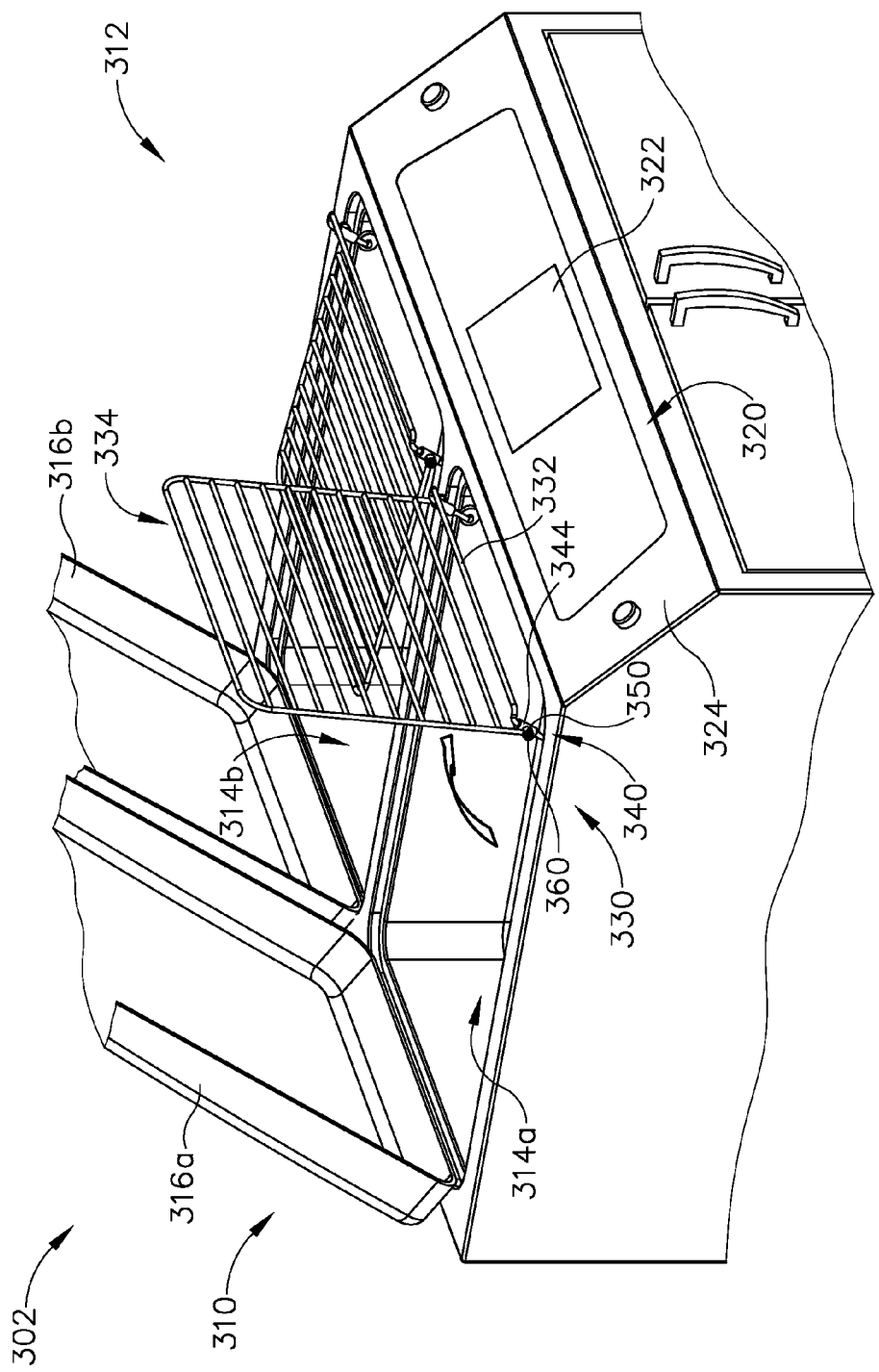
FIG. 9C depicts a perspective view of the reprocessing system of FIG. 4, with the first and second lids in an open configuration, with a first actuating panel assembly in a partially open configuration, and with a second actuating panel assembly in the closed configuration.
Figure 9D:
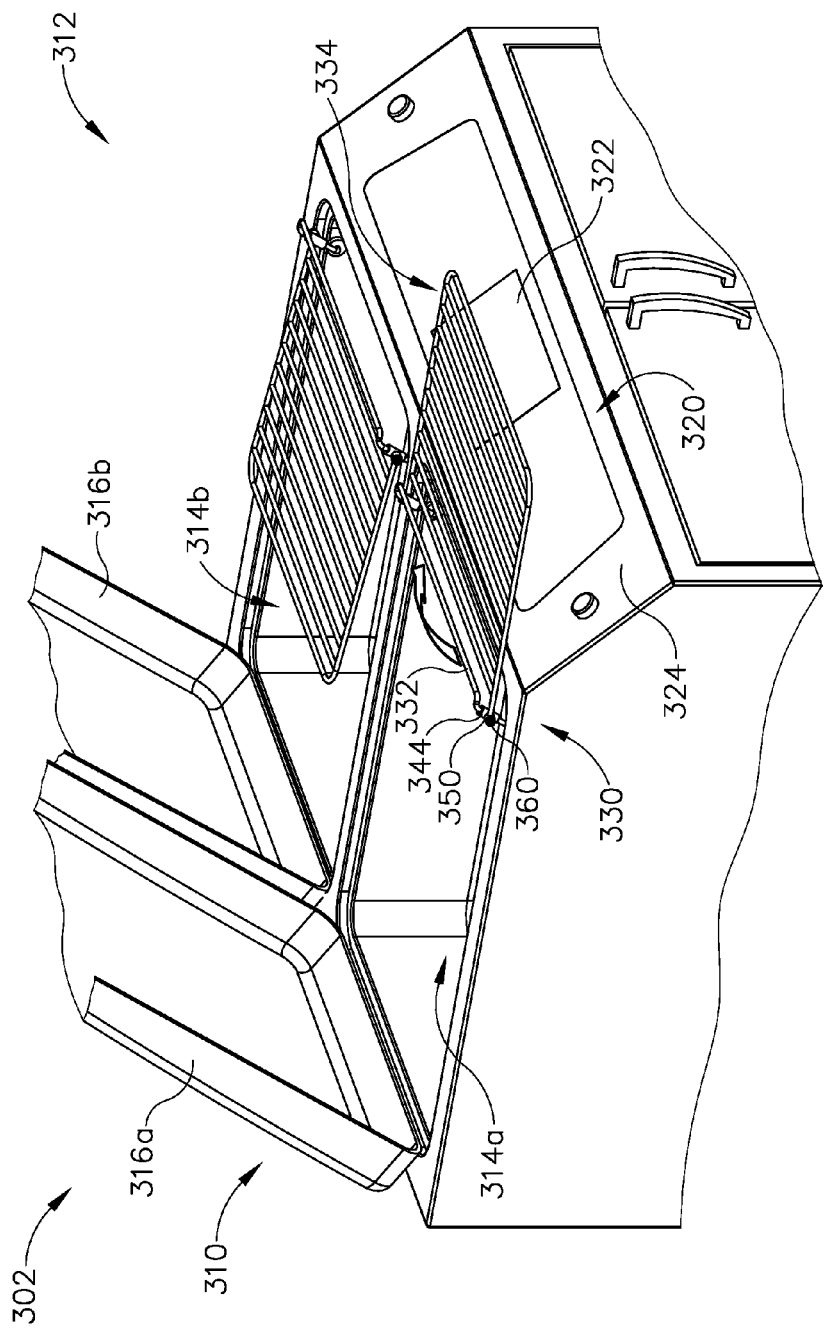
FIG. 9D depicts a perspective view of the reprocessing system of FIG. 4, with the first and second lids in an open configuration, with the first actuating panel assembly in a fully open configuration, and with a second actuating panel assembly in the closed configuration.

As best seen in FIG. 6, latching assembly (340) includes a spring (342), a sleeve (344), a camming member (350), and a shoulder bolt (360). Sleeve (344) defines a longitudinal channel (346) and a lateral threaded channel (348). Longitudinal channel (346) and lateral threaded channel (348) connect with one another. Longitudinal channel (346) is dimensioned to receive a portion of rail (332) while lateral threaded channel (348) is dimensioned to couple with a threaded region (366) of shoulder screw (360). Threaded region (366) of shoulder screw (360) is dimensioned to extend through lateral threaded channel (348) and into longitudinal channel (346), effectively abutting against rail (332). Therefore, shoulder screw (360) is capable of fixing sleeve (344) relative to rail (332).

Camming member (350) is fixed to the ends of peripheral frame (336) of panel (334). As will be described in greater detail below, camming member (350) is configured to pivot relative to sleeve (344) and shoulder screw (360), thereby pivotally coupling panel member (334) to rail (332). Camming member (350) includes an annular wall (352) and an arched surface (354). Camming member (350) defines an opening (356) large enough to receive a shank (362) of shoulder screw (360) adjacent to annular wall (352). Additionally, opening (356) is large enough to receive a head (362) of shoulder screw (360) on the end across from annular wall (352). Camming member (350) includes an arched surface (354) dimensioned to conform to the contours of sleeve (344) in two angular positions, 180 degrees apart. When arched surface (354) conforms to the contours of sleeve (344), panel (334) is positioned so that actuating panel assembly (330) is either in the withdrawn position or the extended position.

Spring (342) receives shank (364) of shoulder screw (360). Ends of spring (342) abut against head (360) of shoulder screw (360) and annular wall (352) of camming member (350). Spring (342) is dimensioned to be compressed between head (360) and annular wall (352). Because shoulder screw (360) is fixed relative to sleeve (344), contact of spring (342) between head (360) and annular wall (352) provides a biasing force against annular wall (352) toward sleeve (344). Spring (342) has sufficient resiliency to bias camming member (350) against sleeve (344) with sufficient force to substantially prevent panel (334) from rotating about latching assembly (340) when arched surface (354) conforms to the contours of sleeve (344). Therefore, latching assembly (340) is capable of allowing actuating panel assembly (330) to be self-supported in both the withdrawn position and the extended position.

However, as will be described in greater detail below, forceful rotation of panel (334) relative to rail (332) may force arched surface (354) to cam against sleeve (344), therefore compressing spring (342) under sufficient force to move camming member (350) toward head (362) of shoulder screw (360) and away from sleeve (344). This movement of camming member (350) away from sleeve (344) allows arched surface (354) to no longer conform to the contours of sleeve (344), thereby unlatching actuating panel assembly (330).

FIGS. 9A-11C show an exemplary process of removing a decontaminated endoscope (200) from reprocessing system (302). First, as shown between FIGS. 9A-9B, lid (316a) is lifted from the closed position to the open position. Then, as shown between FIGS. 9B-9C and FIGS. 11A-11B, an operator may rotate panel (334) of actuating panel assembly (330) from the withdrawn position toward the extended position shown in FIGS. 9D and 11C. As shown between FIGS. 11A-11B, rotation of panel (334) causes arched surface (354) of camming member (350) to cam against sleeve (344). This camming action drives camming member (350) toward head (362) of shoulder bolt (360), which compresses spring (342). It should be understood that actuating panel assembly (330) is not latched into place in the position shown in FIGS. 9C and 10B. Therefore, an operator may more easily pivot panel (334) relative to rail (332) as compared to a latched position. As shown between FIGS. 9C-9D and 11B-11C, panel (334) is further rotated toward the extended position.

While transitioning between FIGS. 9B-9D and 11A-11C, camming member (350) is rotated 180 degrees. Therefore, arched surface (354) now conforms to the contours of sleeve (344) in the position shown in FIGS. 9D and 11C. Spring (342) biases arched surface (354) against sleeve (344), and actuating panel assembly (330) is now latched in the extended position in FIGS. 9D and 11C. As shown in FIG. 10, an operator may then remove a decontaminated endoscope (200) from decontamination basin (314a). As endoscope (200) is being removed, flexible shaft (208) may rest against panel (334) and slide along panel (334) such that there is no cross-contamination between external portions of reprocessing system (302) and endoscope (200). In other words, panel (334) provides a guard preventing flexible shaft (208) from coming into contact with external portions of reprocessing system (302). It should be understood that latching assembly (340) may prevent rotation of panel (334) relative to rail (332) in the event that panel (334) bears any weight of endoscope (200) during removal of endoscope (200).

While in the current example actuating panel assembly (330) rotates from the withdrawn position to the extended position, panel assembly (330) may actuate with latching features in any other suitable manner apparent to one having ordinary skill in the art. For instance, panel (334) may be configured to translate along rails (332) that extend along the length of decontamination basin (14a, 14b), while latching assembly (340) may include resilient tabs and notches in order to latch panel (334) from the withdrawn position to the extended position. It should also be understood that panel (334) may be coupled with lid (316a) such that panel (334) automatically transitions from the closed configuration to the open configuration when lid (316a) transitions from the closed configuration to the open configuration. Similarly, panel (334) may be coupled with lid (316a) such that panel (334) automatically transitions from the open configuration to the closed configuration when lid (316a) transitions from the open configuration to the closed configuration. Various suitable components and arrangements that may be used to provide such a relationship between panel (334) and lid (316a) will be apparent to those of ordinary skill in the art in view of the teachings herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A reprocessing system, comprising: (a) a decontamination basin comprising an interior surface; (b) a lid configured to transition between an open configuration and a closed configuration, wherein the lid is configured to enclose the interior surface of the decontamination basin in the closed configuration, wherein the lid and the interior surface of the decontamination basin are configured to cooperate to house a medical device when in the lid is in the closed configuration; (c) a cleaning assembly operable to clean a medical device housed in the decontamination basin; (d) an exterior body; and (e) an actuating panel assembly, wherein the actuating panel assembly is configured to transition between a withdrawn position and an extended position, wherein the actuating panel assembly is configured to be enclosed by the lid and the interior surface of the decontamination basin in the withdrawn position, wherein the actuating panel assembly is configured to extend above a portion of the exterior body while the actuating panel assembly is in the extended position.

Example 2

The reprocessing system of Example 1, wherein the actuating panel assembly comprises a rail fixed to the interior surface of the decontamination basin.

Example 3

The reprocessing system of Example 2, wherein the actuating panel assembly further comprises a panel configured to actuate relative to the rail from the withdrawn position to the extended position.

Example 4

The reprocessing system of Example 3, wherein the actuating panel assembly further comprises a latching assembly configured to support the panel relative to the rail when the actuating panel assembly is in the withdrawn position or the extended position.

Example 5

The reprocessing system of Example 4, wherein the latching assembly further comprises a sleeve housing a portion of the rail, wherein the sleeve is fixed to the rail.

Example 6

The reprocessing system of Example 5, wherein the latching assembly further comprises a rotating member coupled to the panel.

Example 7

The reprocessing system of Example 6, wherein the latching assembly further comprises a biasing member, wherein the biasing member is configured to bias the rotating member toward the sleeve to support the panel relative to the rail.

Example 8

The reprocessing system of Example 7, wherein the rotating member comprises an arched surface, wherein the arched surface is configured to conform to the contour of the sleeve when the actuating panel assembly is in the withdrawn configuration or the extended configuration.

Example 9

The reprocessing system of any one or more of Examples 7 through 8, wherein the latching assembly further comprises a shoulder bolt configured to fix the sleeve relative to the rail.

Example 10

The reprocessing system of Example 9, wherein the biasing member further comprises a spring, wherein the spring is compresses against the shoulder bolt and the rotating member.

Example 11

The reprocessing system any one or more of Examples 7 through 10, wherein the biasing member is configured to compress in response to rotation of the rotating member.

Example 12

The reprocessing system of any one or more of Examples 5 through 11, wherein the sleeve defines a threaded region, wherein the threaded region is configured to couple with a bolt to fix the sleeve to the rail.

Example 13

The reprocessing system of any one or more of Examples 3 through 12, wherein the panel further comprises a peripheral frame and a plurality of connecting members extending through the peripheral frame.

Example 14

The reprocessing system of any one or more of Examples 2 through 13, wherein the rail comprises a first end and a second end, wherein the first end and the second end are unitarily connected, wherein the first end and the second end are fixed to the interior surface of the decontamination basin.

Example 15

The reprocessing system of any one or more of Examples 1 through 14, wherein the actuating panel assembly is configured to prevent contact between the medical device and a portion of the exterior body below the actuating panel assembly while the actuating panel assembly is in the extended position.

Example 16

A reprocessing system, comprising: (a) a decontamination basin comprising an interior surface defining an opening; (b) a top member configured to transition between an open configuration and a closed configuration, wherein the top member is configured to encompass the opening of the decontamination basin in the closed configuration, wherein the top member and the interior surface of the decontamination basin are configured to house a medical device when the top member is in the closed configuration; (d) a cleaning assembly operable to clean a medical device housed in the decontamination basin; (e) an exterior body, wherein the exterior body is exposed relative to the top member in the closed configuration; and (f) an actuating panel assembly, wherein the actuating panel assembly is configured to transition between a withdrawn position and an extended position when the top member is in the open configuration, wherein the actuating panel assembly is configured to be enclosed by the top member in the closed configuration while the actuating panel assembly is in the withdrawn position, wherein the actuating panel assembly is configured to guard a portion of the exterior body while the actuating panel assembly is in the extended position.

Example 17

The reprocessing system of Example 16, wherein the actuating panel assembly comprises a latching mechanism configured to selectively inhibit movement when the actuating panel assembly is in the withdrawn position or the extended position.

Example 18

The reprocessing system of Example 17, wherein the actuating panel assembly further comprises a rack configured to prevent contact between the surgical equipment and a portion of the exterior body underneath the rack while the actuating panel is in the extended position.

Example 19

The reprocessing system of Example 18, wherein the rack is configured to rotate relative to the decontamination basin.

Example 20

A reprocessing system, comprising: (a) a decontamination basin comprising an interior surface defining an opening; (b) a top member configured to transition between an open configuration and a closed configuration, wherein the top member is configured to encompass the opening of the decontamination basin in the closed configuration, wherein the top member and the interior surface of the decontamination basin are configured to house a medical device when the top member is in the closed configuration; (d) a cleaning assembly operable to clean a medical device housed in the decontamination basin; (e) an exterior body, wherein the exterior body is exposed relative to the top member in the closed configuration; and (f) an actuating panel assembly comprising a grate configured to fit between the top member and the interior surface of the decontamination basin while the top member s in the closed configuration, where the grate is configured to extend over a portion of the exterior body while the top member is in the open configuration.

V. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A reprocessing system, comprising:
   (a) a decontamination basin defining an opening, wherein the decontamination basin comprises an interior surface;
   (b) a lid configured to transition between an open configuration and a closed configuration, wherein the lid is configured to enclose the opening and the interior surface of the decontamination basin in the closed configuration, wherein the lid and the interior surface of the decontamination basin are configured to cooperate to house a medical device when in the lid is in the closed configuration;
   (c) a cleaning assembly operable to clean a medical device housed in the decontamination basin;
   (d) an exterior body having a front region, wherein the decontamination basin is behind the front region; and
   (e) an actuating panel assembly comprising a panel, wherein the actuating panel assembly is configured to transition between a withdrawn position and an extended position, wherein the panel is configured to be enclosed by the lid and the interior surface of the decontamination basin in the withdrawn position, wherein the actuating panel assembly is configured to fit between the lid and the interior surface of the decontamination basin while the lid is in the closed configuration, wherein the panel is configured to extend over the front region of the exterior body and in front of the decontamination basin while the actuating panel assembly is in the extended position.

2. The reprocessing system of claim 1, wherein the actuating panel assembly is configured to prevent contact between the medical device and a portion of the exterior body below the actuating panel assembly while the actuating panel assembly is in the extended position.

3. The reprocessing system of claim 1, wherein the actuating panel assembly comprises a rail fixed to the interior surface of the decontamination basin.

4. The reprocessing system of claim 3, wherein the rail comprises a first end and a second end, wherein the first end and the second end are unitarily connected, wherein the first end and the second end are fixed to the interior surface of the decontamination basin.

5. The reprocessing system of claim 3, wherein the actuating panel assembly further comprises a panel configured to actuate relative to the rail from the withdrawn position to the extended position.

6. The reprocessing system of claim 5, wherein the panel further comprises a peripheral frame and a plurality of connecting members extending through the peripheral frame.

7. The reprocessing system of claim 5, wherein the actuating panel assembly further comprises a latching assembly configured to support the panel relative to the rail when the actuating panel assembly is in the withdrawn position or the extended position.

8. The reprocessing system of claim 7, wherein the latching assembly further comprises a sleeve housing a portion of the rail, wherein the sleeve is fixed to the rail.

9. The reprocessing system of claim 8, wherein the sleeve defines a threaded region, wherein the threaded region is configured to couple with a bolt to fix the sleeve to the rail.

10. The reprocessing system of claim 8, wherein the latching assembly further comprises a rotating member coupled to the panel.

11. The reprocessing system of claim 10, wherein the latching assembly further comprises a biasing member, wherein the biasing member is configured to bias the rotating member toward the sleeve to support the panel relative to the rail.

12. The reprocessing system of 11, wherein the biasing member is configured to compress in response to rotation of the rotating member.

13. The reprocessing system of claim 11, wherein the rotating member comprises an arched surface, wherein the arched surface is configured to conform to the contour of the sleeve when the actuating panel assembly is in the withdrawn configuration or the extended configuration.

14. The reprocessing system of claim 11, wherein the latching assembly further comprises a shoulder bolt configured to fix the sleeve relative to the rail.

15. The reprocessing system of claim 14, wherein the biasing member further comprises a spring, wherein the spring is compresses against the shoulder bolt and the rotating member.

16. A reprocessing system, comprising:
   (a) a decontamination basin comprising an interior surface defining an opening;
   (b) a top member configured to transition between an open configuration and a closed configuration, wherein the top member is configured to encompass the opening of the decontamination basin in the closed configuration, wherein the top member and the interior surface of the decontamination basin are configured to house a medical device when the top member is in the closed configuration;
   (c) a cleaning assembly operable to clean a medical device housed in the decontamination basin;
   (d) an exterior body, wherein the exterior body is exposed relative to the top member in the closed configuration; and
   (e) an actuating panel assembly, wherein the actuating panel assembly is configured to transition between a withdrawn position and an extended position when the top member is in the open configuration, wherein the actuating panel assembly is configured to be enclosed by the top member in the closed configuration while the actuating panel assembly is in the withdrawn position, wherein the actuating panel assembly is configured to be disposed between the top member and the medical device while the medical device is in the decontamination basin and the actuating panel assembly is in the withdrawn position, wherein the actuating panel assembly is configured to guard a portion of the exterior body while the actuating panel assembly is in the extended position.

17. The reprocessing system of claim 16, wherein the actuating panel assembly comprises a latching mechanism comprises an arched surface.

18. The reprocessing system of claim 17, wherein the actuating panel assembly further comprises a rack configured to prevent contact between the medical device and a portion of the exterior body underneath the rack while the actuating panel is in the extended position.

19. The reprocessing system of claim 18, wherein the rack is configured to rotate relative to the decontamination basin.

20. A reprocessing system, comprising:
(a) a decontamination basin comprising an interior surface defining an opening;
(b) a top member configured to transition between an open configuration and a closed configuration, wherein the top member is configured to encompass the opening of the decontamination basin in the closed configuration, wherein the top member and the interior surface of the decontamination basin are configured to house a medical device when the top member is in the closed configuration;
(d) a cleaning assembly operable to clean a medical device housed in the decontamination basin;
(e) an exterior body, wherein the exterior body is exposed relative to the top member in the closed configuration; and
(f) an actuating panel assembly comprising a grate configured to extend proximally relative to a front portion of the exterior body and fit between the top member and the interior surface of the decontamination basin while the top member is in the closed configuration, wherein the grate is configured to extend distally relative to the front portion of the exterior body while the top member is in the open configuration.

* * * * *